(12) United States Patent
Suddaby

(10) Patent No.: US 11,580,268 B2
(45) Date of Patent: Feb. 14, 2023

(54) METHOD OF CREATING A CUSTOMIZED SEGMENTED ALIGNMENT ROD FOR ALIGNMENT OF A SPINE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 339 days.

(21) Appl. No.: 16/901,193

(22) Filed: Jun. 15, 2020

(65) Prior Publication Data

US 2020/0311318 A1    Oct. 1, 2020

Related U.S. Application Data

(63) Continuation-in-part of application No. 16/802,695, filed on Feb. 27, 2020, now Pat. No. 11,317,949, (Continued)

(51) Int. Cl.
| | | |
|---|---|---|
| *A61B 34/00* | (2016.01) | |
| *G06F 30/10* | (2020.01) | |
| *G16H 30/20* | (2018.01) | |
| *G16H 70/60* | (2018.01) | |
| *G16H 50/50* | (2018.01) | |
| *G16H 50/20* | (2018.01) | |
| *A61B 17/70* | (2006.01) | |

(Continued)

(52) U.S. Cl.
CPC .......... *G06F 30/10* (2020.01); *A61B 17/7029* (2013.01); *A61B 34/10* (2016.02); *G01B 11/022* (2013.01); *G16H 30/20* (2018.01); *G16H 30/40* (2018.01); *G16H 50/20* (2018.01); *G16H 50/50* (2018.01); *G16H 70/60* (2018.01); *A61B 17/7002* (2013.01); *A61B 2017/00526* (2013.01); *A61B 2017/681* (2013.01); *A61B 2034/102* (2016.02); *G06F 2111/02* (2020.01); *G06Q 50/04* (2013.01)

(58) Field of Classification Search
CPC ..... A61B 17/8863; A61B 34/00; A61B 34/10; A61B 34/20; G06F 30/10
See application file for complete search history.

(56) References Cited

U.S. PATENT DOCUMENTS

| | | |
|---|---|---|
| 5,290,289 A | 3/1994 | Sanders et al. |
| 5,649,925 A | 7/1997 | Barbera Alacreu |

(Continued)

FOREIGN PATENT DOCUMENTS

| | | |
|---|---|---|
| CN | 207150033 U | 3/2018 |
| WO | WO2007/086053 | 8/2007 |

(Continued)

OTHER PUBLICATIONS https://www.medicrea.com/usa/th-lumbar-range-usa/ib3e-tb. "IB3D-TB", last accessed Jul. 16, 2018.

(Continued)

*Primary Examiner* — Olivia C Chang
(74) *Attorney, Agent, or Firm* — Harter Secrest & Emery LLP; Michael Nicholas Vranjes

(57) ABSTRACT

A method for creating a segmented alignment rod, the method including receiving a request for a segmented alignment rod, receiving at least one image of a deformed spine, generating, a normal spinal curvature, and generating a segmented alignment rod design.

13 Claims, 12 Drawing Sheets

Related U.S. Application Data which is a continuation-in-part of application No. 15/962,145, filed on Apr. 25, 2018, now Pat. No. 10,624,683.

(51) Int. Cl.

| | | |
|---|---|---|
| *G01B 11/02* | (2006.01) | |
| *G16H 30/40* | (2018.01) | |
| *A61B 34/10* | (2016.01) | |
| *A61B 17/00* | (2006.01) | |
| *G06Q 50/04* | (2012.01) | |
| *G06F 111/02* | (2020.01) | |
| *A61B 17/68* | (2006.01) | |

(56) References Cited

U.S. PATENT DOCUMENTS

| | | |
|---|---|---|
| 5,879,352 A | 3/1999 | Filoso et al. |
| 6,296,644 B1 | 10/2001 | Saurat et al. |
| 6,607,530 B1 | 8/2003 | Carl et al. |
| 7,410,489 B2 | 8/2008 | Dakin et al. |
| 7,634,874 B2 | 12/2009 | Lucas |
| 7,766,941 B2 | 8/2010 | Paul |
| 7,785,325 B1 | 8/2010 | Milbank |
| 8,105,360 B1 | 1/2012 | Connor |
| 8,133,241 B2 | 3/2012 | Boyd et al. |
| 8,206,423 B2 | 6/2012 | Siegal |
| 8,353,935 B2 | 1/2013 | Krause |
| 8,398,633 B2 | 3/2013 | Mueller |
| 8,685,022 B2 | 4/2014 | Lorenz et al. |
| 8,709,042 B2 | 4/2014 | Greenhalgh et al. |
| 8,768,509 B2 | 7/2014 | Unsworth |
| 8,845,690 B2 | 9/2014 | Capozzoli |
| 9,050,112 B2 | 6/2015 | Greenhalgh et al. |
| 9,113,783 B2 | 8/2015 | Suehara |
| 9,144,506 B2 | 9/2015 | Phelps |
| 9,221,179 B2 | 12/2015 | Hinman |
| 9,339,298 B1 | 5/2016 | Morales Chavarria |
| 9,504,307 B1 | 11/2016 | Burnett et al. |
| 9,592,132 B2 | 3/2017 | Hauck et al. |
| 9,642,712 B2 | 5/2017 | Schaller et al. |
| 9,668,641 B2 | 6/2017 | Ostrovsky et al. |
| 9,763,678 B2 | 9/2017 | O'Neil et al. |
| 2005/0262911 A1* | 12/2005 | Dankowicz ........ A61B 17/8863 72/31.04 |
| 2006/0058801 A1 | 3/2006 | Schlienger et al. |
| 2008/0234691 A1 | 9/2008 | Schwab |
| 2008/0294163 A1 | 11/2008 | Chou et al. |
| 2009/0012565 A1 | 1/2009 | Sachs et al. |
| 2009/0112262 A1 | 4/2009 | Pool et al. |
| 2009/0118771 A1 | 5/2009 | Gonzlez-Hernandez |
| 2009/0216232 A1 | 8/2009 | Buford, II et al. |
| 2009/0228007 A1 | 9/2009 | Justin et al. |
| 2009/0228008 A1 | 9/2009 | Justin et al. |
| 2010/0331842 A1 | 12/2010 | Milbank |
| 2011/0144703 A1 | 6/2011 | Krause et al. |
| 2013/0103091 A1 | 4/2013 | Acosta, Jr. et al. |
| 2013/0325007 A1 | 12/2013 | Beyar et al. |
| 2015/0257800 A1 | 9/2015 | Harshman et al. |
| 2018/0353214 A1 | 12/2018 | Kiester |
| 2019/0328424 A1 | 10/2019 | Suddaby |

FOREIGN PATENT DOCUMENTS

| | | |
|---|---|---|
| WO | WO2016/166663 | 10/2016 |
| WO | WO2017/201437 | 11/2017 |

OTHER PUBLICATIONS

Brochure. "ZIP Product Line, MIS Interspinous Fusion Systems", Surgical Technique Guide, Aurora Spine, Carlsbad, California, aurora-spine.com, 2014.

Mueller, Christian W. et al. "A Novel Shape Memory Plate Osteosynthesis for Noninvasive Modulation of Fixation Stiffness in a Rabbit Tibia Osteotomy Model", Hindawi Publishing Corporation, BioMed Research International, vol. 2015, Article ID 652940, 8 Pages, Http://dx.doi.org.

Barbosa, Lorena Monterio Cavalcanti et al. "Thermal Simulation of Electrical Heating of Shape Memory Alloys Wires Into a Polymeric Matrix With Two Different Sequences of Activation", 21st Brazilian Congress of Mechanical Engineering, Oct. 24-28, 2011, Natl, RN, Brazil.

Ali, Mohamed et al. "Selective RF wireless control of integrated bulk-micromachined shape-memory-alloy actuators and it's microfluidic application", Universiti Teknologi Malaysia Institutional Repository, Proceedings of the IEEE International Conference on Micro Electro Mechanical Systems (MEMS). IEEE, Cancun, http://eprints.utm.my/ID/eprint/29590., 2011, pp. 1269-1272.

\* cited by examiner

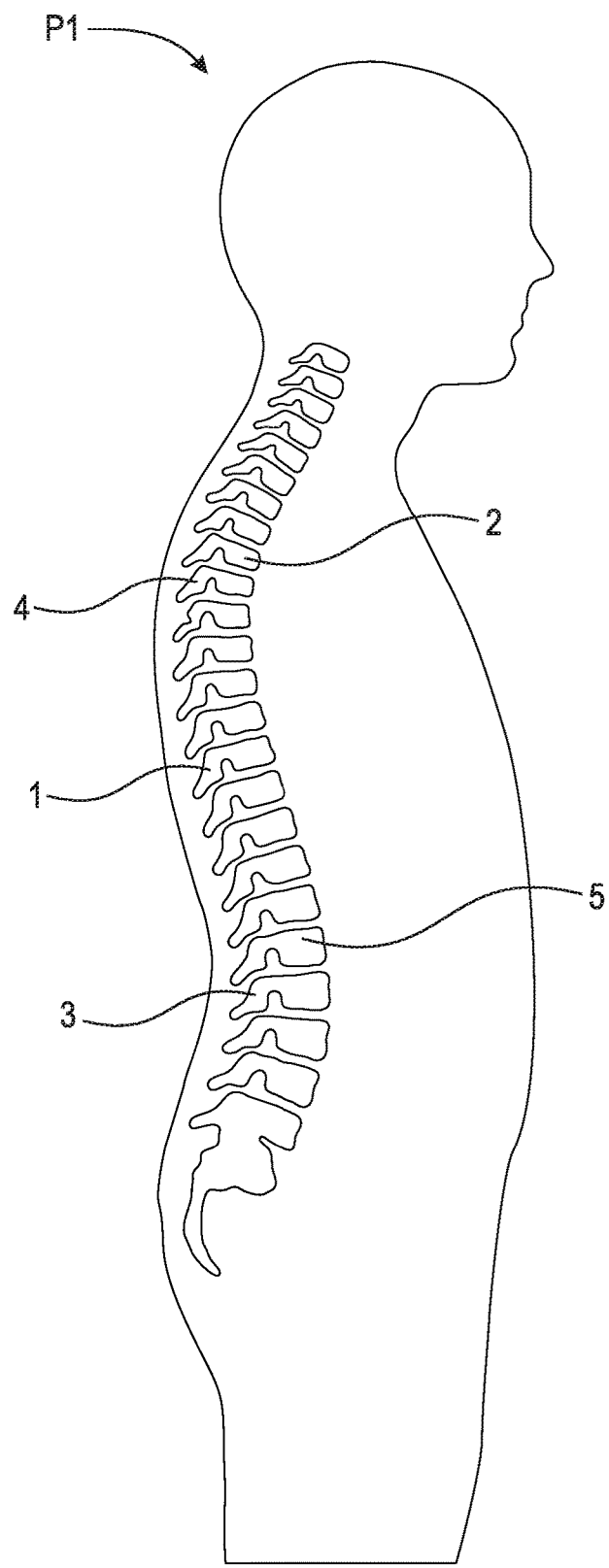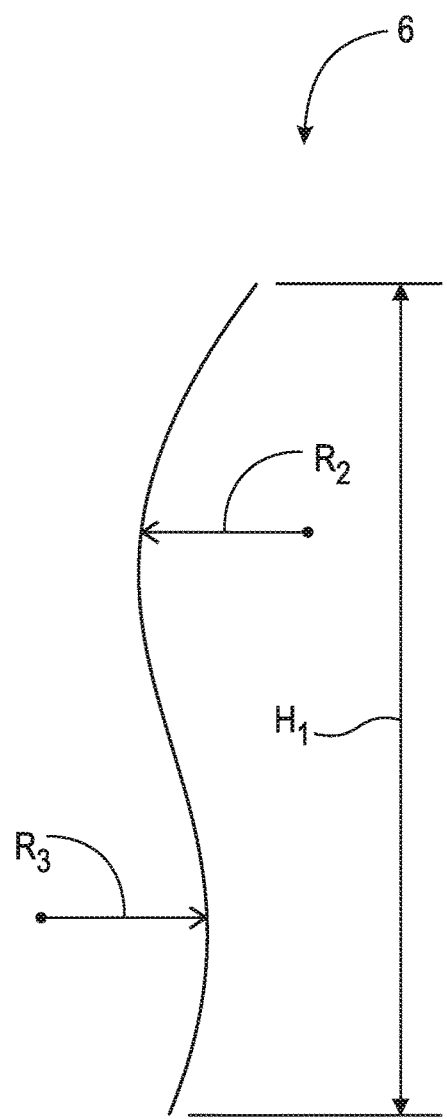
Fig. 4A
Fig. 4B

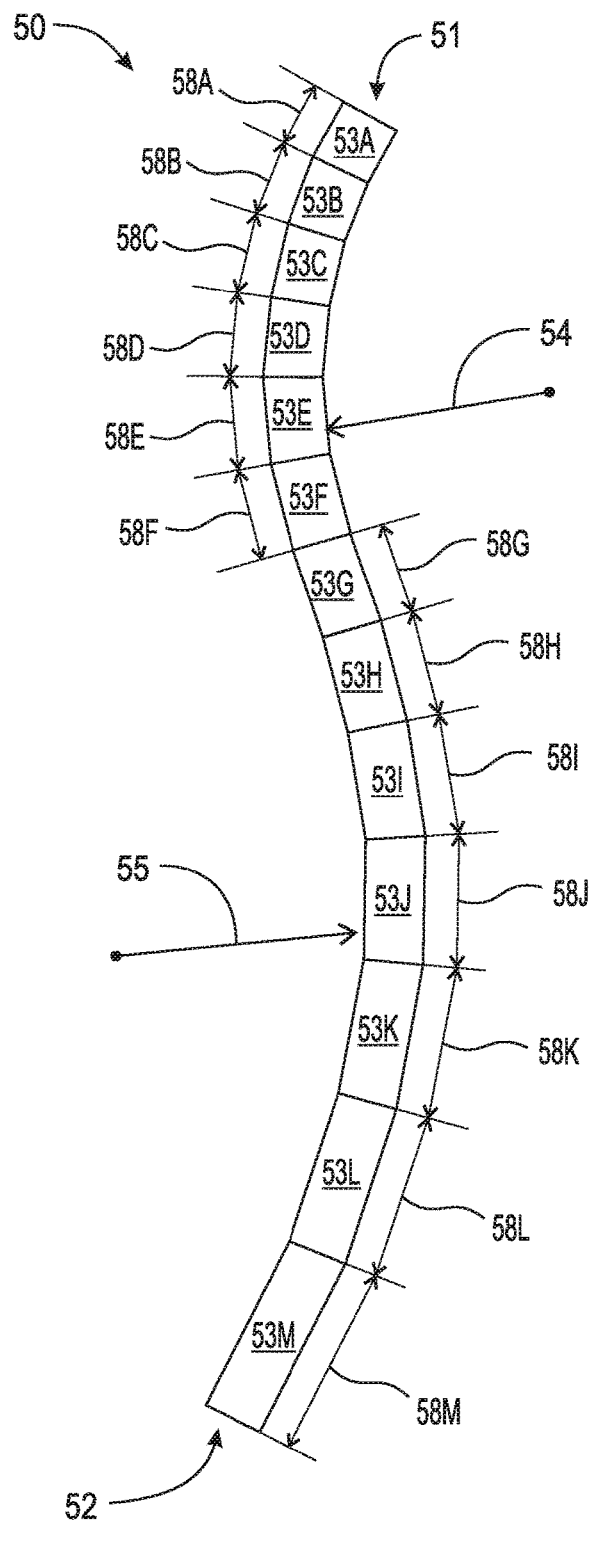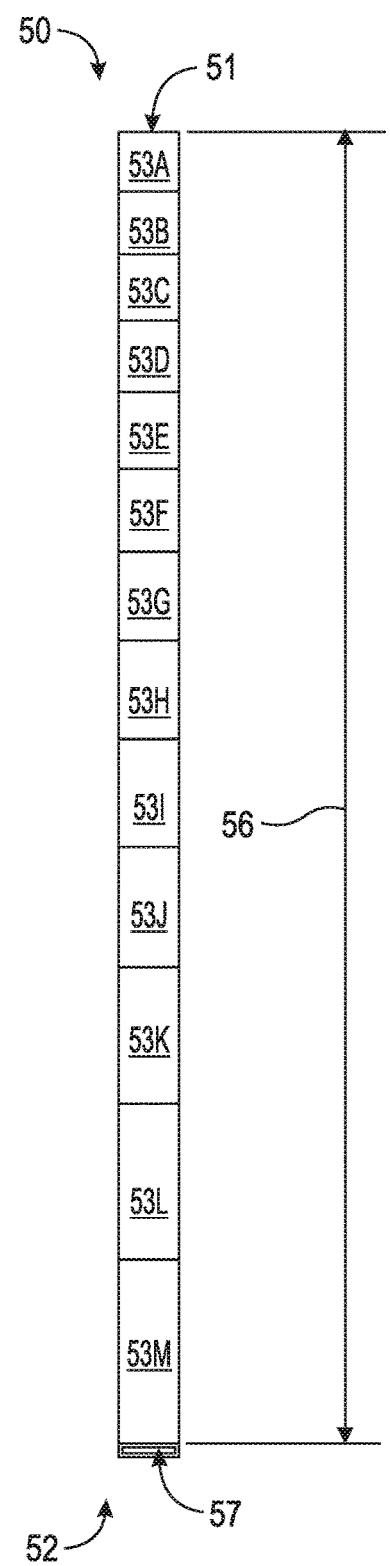
Fig. 10A
Fig. 10B

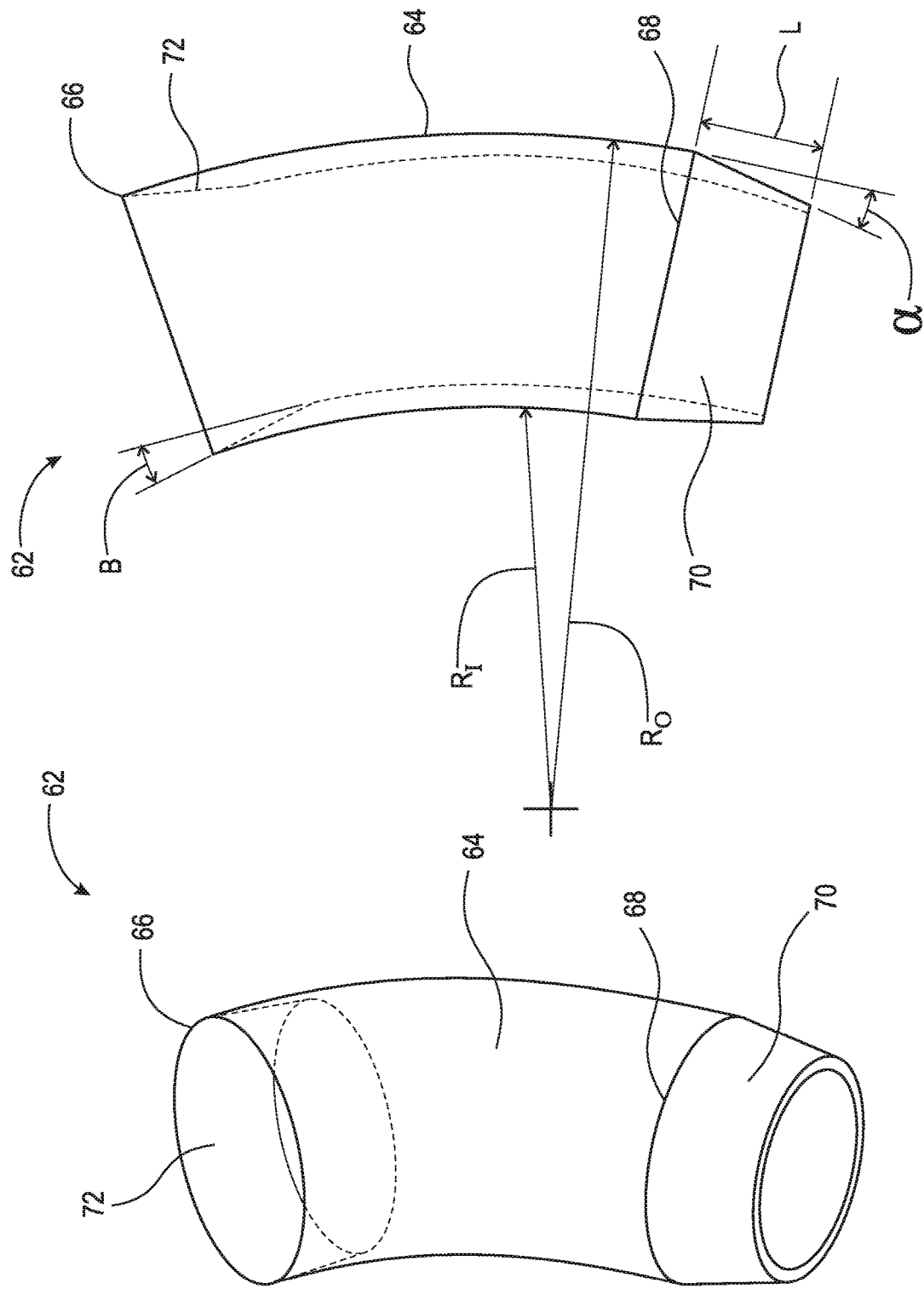

METHOD OF CREATING A CUSTOMIZED SEGMENTED ALIGNMENT ROD FOR ALIGNMENT OF A SPINE

CROSS-REFERENCE TO RELATED APPLICATIONS

This application is filed under 35 U.S.C. § 120 as a continuation-in-part of U.S. patent application Ser. No. 16/802,695, filed on Feb. 27, 2020, which application is a continuation-in-part of U.S. patent application Ser. No. 15/962,145, filed on Apr. 25, 2018, now U.S. Pat. No. 10,624,683, which references are hereby incorporated by reference in their entireties.

FIELD

The present disclosure relates to spinal alignment, and more particularly to a method for creating a customized segmented alignment rod assembly for performing a gradual three-dimensional alignment of a spine which has deviated from a normal attitude for pathologic reasons.

BACKGROUND

Scoliosis is a disorder that causes an abnormal curve of the spine, or backbone. Patients with scoliosis develop abnormal curves to either side of the body's median line (lateral curve) and the bones of the spine twist on each other like a corkscrew.

The Greek physician Hippocrates coined the term scoliosis and devised various forms of external braces and benches to support or stretch the abnormally curved spine. Since animals can also suffer from scoliosis, there is little doubt it is an anomaly that has been around since the dawn of vertebrates. It is estimated that about 3% of humans are afflicted, meaning over 200 million people worldwide are living with this anomaly.

Females are much more likely to suffer from scoliosis than males and for idiopathic scoliosis the ratio is 10:1, respectively. Scoliosis can be seen at any age, but it is most common in those over ten years old. Present knowledge suggests a genetically predisposed growth asymmetry at the level of the vertebral body endplates as a potential underlying cause.

Minor degrees of scoliosis are treated with bracing or stretching of the spine, not that dissimilar to the prescriptions and descriptions dating back to the time of Hippocrates. While the materials and techniques have changed, the principals have evolved very little.

Severe degrees of scoliosis are largely treated by a major operation known as segmental instrumented spinal fusion, a lengthy procedure where the muscles are flayed from the spinal bone and metal rods are then implanted to straighten the spine and hold it in position until grafted bone products fuse the spinal vertebrae together into a solid tower of bone. Since the normal spine is segmented to permit functional motion, fusion in and of itself sets the stage for life long corollary problems directly related to the administered cure which precludes normal movement, and at times, even normal growth.

Because of the magnitude of the surgery, complications include death, paralysis, infection, and hardware failure. Late complications include stiffness, chronic back pain, late hardware failure, and breakdown of adjacent normal segments because of stress provided by the long fused spinal segment. This list of complications is illustrative and not exhaustive.

Since major scoliosis surgery is such a cataclysmic event, it is often employed as a last resort, meaning that simple curves are followed until major curves develop thereby increasing not only the magnitude of the surgery, but the potential risk of complications as well.

Present scoliosis treatment is rather eclectic, employing everything from techniques of bracing, essentially outlined in the time of Hippocrates, to the major robotic surgeries of present day. As with anything in medicine, whenever multiple solutions exist for a particular disease process, it generally means that no single solution is sufficiently effective.

Other spinal deformities include kyphosis, lordosis, and flatback. Kyphosis, lordosis, and flatback include deformities in the natural curvature of the spine, from a lateral view, or in the sagittal (front to back) plane, whereas scoliosis includes deformities in the straight-line arrangement of the spine, from a posterior view, or in the frontal (side to side) plane.

Kyphosis is an exaggerated, forward rounding of the back, and can occur at any age but is most common in older women. Age-related kyphosis is often due to weakness in the spinal bones that causes them to compress or crack. Other types of kyphosis can appear in infants or teens due to malformation of the spine or wedging of the spinal bones over time.

Lordosis is defined as an excessive inward curve of the spine. Lordosis is found in all age groups and it primarily affects the lumbar spine, but can occur in the neck (cervical). When found in the lumbar spine, the patient may appear swayback, with the buttocks more prominent, and in general an exaggerated posture. Lumbar lordosis can be painful and sometimes affect movement.

Flatback syndrome is a condition in which the lower spine loses some of its normal curvature. Normally, the spine has several gentle front-to-back curves. The lumbar (lower) spine has a lordosis, or inward curve. The thoracic (middle) spine has a kyphosis, or outward curve, and the cervical spine (neck) has a lordosis. These curves work in harmony to keep the body's center of gravity aligned over the hips and pelvis. If the lumbar lordosis is lost, the center of gravity can be put too far forward. This is the case in flatback syndrome.

Clearly, there is a need in the art to have a treatment that is simple and safe enough to employ such that spinal curvatures can be treated early in the pathologic process so that progression to major curvature can be avoided along with the attendant major interventional surgery required when the curves are extreme. There is also a need in the art to diminish or eradicate the requirement for fusing the spine such that normal motion can be maintained, and the deleterious consequence of a spinal fusion avoided. Additionally, there is a need in the art to develop a customized treatment based on the patient's size, age, sex, and extent of the spinal deformity, such that the treatment is optimized on a patient-by-patient basis.

SUMMARY

According to aspects illustrated herein, there is provided a method for creating a segmented alignment rod, the method comprising receiving, by one or more computer processors, a request for a segmented alignment rod, receiving, by the one or more computer processors, at least one image of a deformed spine, generating, by the one or more computer processors, a normal spinal curvature, and generating, by the one or more computer processors, a segmented alignment rod design.

In some embodiments, the method further comprises sending, by the one or more computer processors, the segmented alignment rod design to a segmented alignment rod creation machine. In some embodiments, the method further comprises, after the step of receiving the at least one image of the deformed spine, processing, by the one or more computer processors, the at least one image of the deformed spine. In some embodiments, the step of processing the at least one image of the deformed spine comprises measuring, by the one or more computer processors, the deformed spine. In some embodiments, the step of measuring the deformed spine comprises measuring, by the one or more computer processors, one or more vertebra and one or more discs of the deformed spine, and measuring, by the one or more computer processors, a curvature of the deformed spine. In some embodiments, the step of processing the at least one image of the deformed spine comprises measuring, by the one or more computer processors, one or more vertebra and one or more discs of the deformed spine, and measuring, by the one or more computer processors, a curvature of the deformed spine. In some embodiments, the step of generating the segmented alignment rod design comprises, based on the at least one image received, determining, by the one or more computer processors, a number of segments in the segmented alignment rod design, and based on the measurements and the normal spinal curvature, determining, by the one or more computer processors, a curvature of each of the segments. In some embodiments, the step of generating the segmented alignment rod design comprises, based on the at least one image received, determining, by the one or more computer processors, a number of segments in the segmented alignment rod design, and based on the measurements, determining, by the one or more computer processors, a male engaging element shape and a female engaging element shape for each of the segments. In some embodiments, the step of generating the segmented alignment rod design comprises, based on the at least one image received, determining, by the one or more computer processors, a number of segments in the segmented alignment rod design, and based on the measurements, determining, by the one or more computer processors, a length of each of the segments. In some embodiments, the step of generating the segmented alignment rod design comprises, based on the at least one image received, determining, by the one or more computer processors, a number of segments in the segmented alignment rod design and a length of each of the segments. In some embodiments, the step of generating the segmented alignment rod design further comprises estimating, by the one or more computer processors, a total length of growth of the deformed spine, and based on the measurements and the estimated total length of growth, determining, by the one or more computer processors, the length of each of the segments. In some embodiments, the step of receiving the request for the segmented alignment rod comprises, receiving, by the one or more computer processors, data related to a patient. In some embodiments, the data comprises an age and height. In some embodiments, the step of generating the normal spinal curvature comprises comparing, by the one or more computer processors, the data to a plurality of normal spinal curvatures in a database, selecting, by the one or more computer processors, one spinal curvature of the plurality of normal spinal curvatures, and generating, by the one or more computer processors, the normal spinal curvature based on dimensions of the selected normal spinal curvature.

According to aspects illustrated herein, there is provided a computer system for creating a segmented alignment rod, comprising an imaging machine, one or more computer processors, one or more computer readable storage media, program instructions stored on the computer readable storage media for execution by at least one or more computer processors, the program instructions comprising program instructions to receive a request for a segmented alignment rod, program instructions to receive at least one image of a deformed spine from the imaging machine, program instructions to generate a normal spinal curvature, and program instructions to generate a segmented alignment rod design.

In some embodiments, the computer system further comprises program instructions to send the segmented alignment rod design to a segmented alignment rod creation machine. In some embodiments, the program instructions to receive the at least one image of the deformed spine comprise program instructions to receive the at least one image of the deformed spine, program instructions to measure one or more vertebra and one or more discs of the deformed spine, and program instructions to measure a curvature of the deformed spine. In some embodiments, the program instructions to generate the segmented alignment rod design comprise program instructions to, based on the at least one image received, determine a number of segments in the segmented alignment rod design, and program instructions to, based on the measurements, determine a length of each of the segments. In some embodiments, the program instructions to generate the segmented alignment rod design comprise program instructions to, based on the at least one image received, determine a number of segments in the segmented alignment rod design and a length of each of the segments. In some embodiments, the program instructions to receive the request for the segmented alignment rod comprise program instructions to receive data related to a patient. In some embodiments, the program instructions to generate the normal spinal curvature comprise program instructions to compare the data to a plurality of normal spinal curvatures in a database, program instructions to select one spinal curvature of the plurality of normal spinal curvatures, and program instructions to generate the normal spinal curvature based on dimensions of the selected normal spinal curvature.

According to aspects illustrated herein, there is provided a computer program product for creating a segmented alignment rod, comprising an imaging machine, a computer readable storage medium and program instructions stored on the computer readable storage medium, the program instructions comprising program instructions to receive a request for a segmented alignment rod, program instructions to receive at least one image of a deformed spine from the imaging machine, program instructions to process the at least one image to obtain dimensions of the deformed spine, program instructions to, based at least partially on the request, generate a normal spinal curvature, and program instructions to, based at least partially on the dimensions and the normal spinal curvature, generate a segmented alignment rod design.

In some embodiments, the program instructions to process the at least one image comprise program instructions to measure one or more vertebra and one or more discs of the deformed spine, and program instructions to measure a curvature of the deformed spine. In some embodiments, the program instructions to receive a request for the segmented alignment rod comprise program instructions to receive an age and height of a patient.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 4A is a stylized lateral view of a person with a normal spine;

FIG. 4B is a line indicating the sagittal curvature of the spine shown in FIG. 4A;

FIG. 10A is a lateral elevational view of a segmented alignment rod;

FIG. 10B is a posterior elevational view of the segmented alignment rod shown in FIG. 10A;

FIG. 11A is a perspective view of a segment of a segmented alignment rod;

FIG. 11B is a side elevational view of the segment shown in FIG. 11A;

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be appreciated that the apex vertebra, apex, or apex of the curve is the vertebra or disk with the greatest rotation or farthest deviation from the center of the vertebral column. End vertebrae are those with the maximal tilt toward the apex of the curve. "Marked vertebra" as used herein is meant to indicate the vertebra (or vertebrae) which needs to travel the furthest in order that the spinal column be properly aligned according to a normal curvature, or a vertebra (or vertebrae) that is deemed essential in properly aligning the spinal column to a normal curvature.

Figure 1:
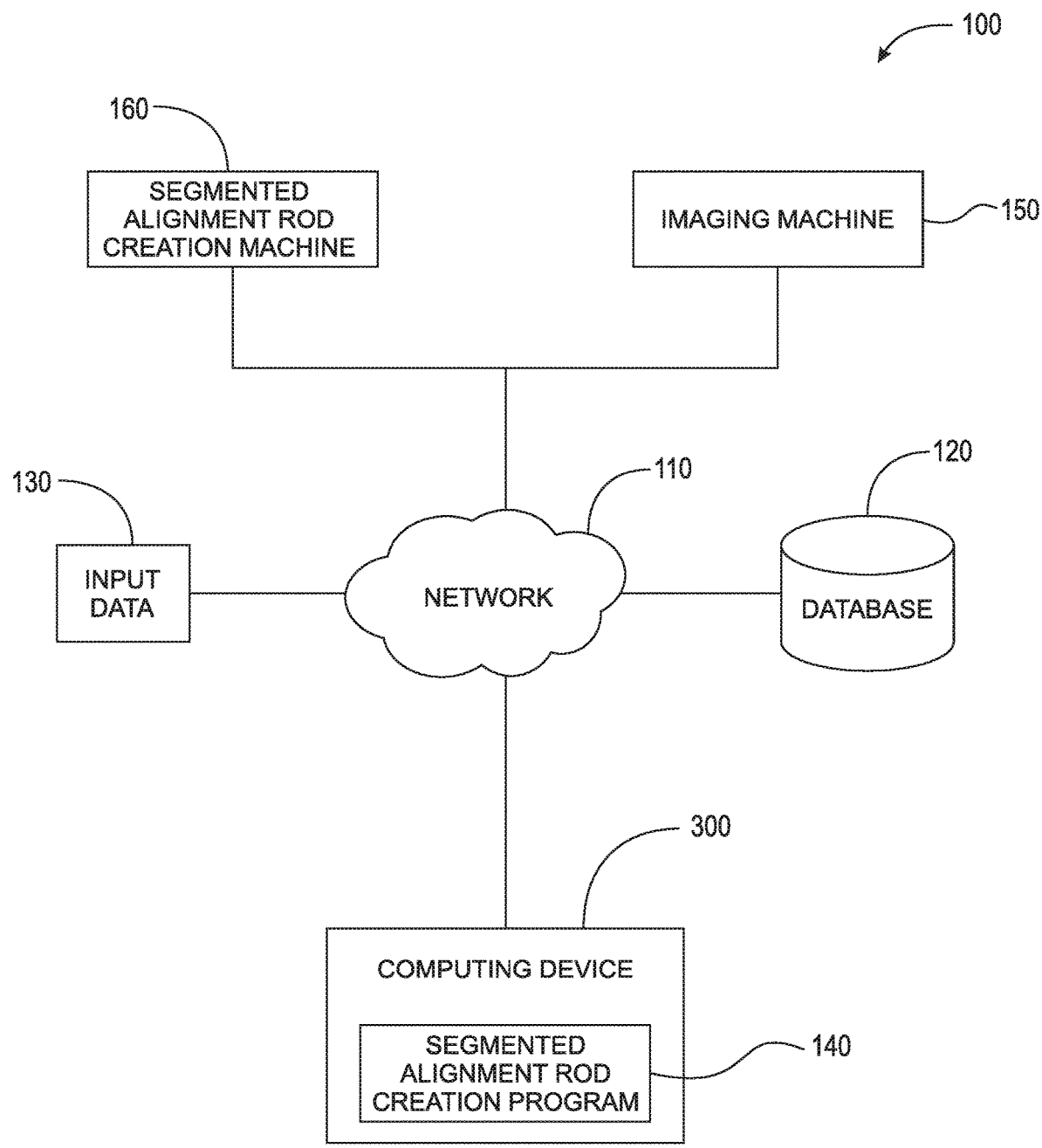
FIG. 1 is a functional block diagram illustrating an environment, in accordance with some embodiments of the present disclosure.

Referring now to the figures, FIG. 1 is a functional block diagram illustrating a segmented alignment rod creation environment, generally designated 100, in accordance with some embodiments of the present disclosure. FIG. 1 provides only an illustration of one implementation, and does not imply any limitations with regard to the environments in which different embodiments may be implemented. Many modifications to the depicted environment may be made by those skilled in the art without departing from the scope of the disclosure as recited by the claims. In some embodiments, segmented alignment rod creation environment 100 includes computing device 300, database 120, and input record data 130, imaging machine 150, and segmented alignment rod creation machine 160, all of which are connected to network 110.

Network 110 can be, for example, a local area network (LAN), a wide area network (WAN) such as the Internet, or a combination of the two, and can include wired, wireless, or fiber optic connections.

Computing device 300 may be a hardware device that produces a customized segmented alignment rod design using segmented alignment rod creation program 140. Computing device 300 is capable of communicating with network 110, database 120, input record data 130, imaging machine 150, and segmented alignment rod creation machine 160. In some embodiments, computing device 300 may include a computer. In some embodiments, computing device 300 may include internal and external hardware components, as depicted and described in further detail with respect to FIG. 3. In some embodiments, segmented alignment rod creation program 140 is implemented on a web server, which may be a management server, a web server, or any other electronic device or computing system capable of receiving and sending data. The web server can represent a computing system utilizing clustered computers and components to act as a single pool of seamless resources when accessed through a network. The web server may include internal and external hardware components, as depicted and described in further detail with respect to FIG. 3.

Segmented alignment rod creation program 140 receives requests for customized segmented alignment rods. Segmented alignment rod creation program 140 can receive requests for a custom segmented alignment rod based on, inter alia, various criteria, such as patient age, sex, height, weight, spinal column imagery, and desired curvature, generate a custom segmented alignment rod design, and create a custom segmented alignment rod by communicating with segmented alignment rod creation machine 160. Segmented alignment rod creation program 140 can generally include any software capable generating a custom segmented alignment rod design and utilizing a segmented alignment rod creation machine to create the custom segmented alignment rod according to the present disclosure and communicating with database 120, input record data 130, imaging machine 150, and segmented alignment rod creation machine 160 over network 110.

Database 120 is a central storage for a set of spinal column parameters. Database 120 can be implemented using any non-volatile storage medium known in the art. For example, authentication database can be implemented with a tape library, optical library, one or more independent hard disk drives, or multiple hard disk drives in a redundant array of independent disks (RAID). In some embodiments, database 120 may contain a set of parameters related to spinal column curvature. For example, a 6 year-old boy that is 45.5" tall, weighs 44 pounds, and has a normal spinal column 1 might have an upper radius $R_2$ and a lower radius $R_3$ (see FIGS. 4A-5B) These dimensions might be used as the basis to generate a segmented alignment rod for a patient around 6-years old that is 48" tall, weighs 42 pounds, and kyphosis. Thus, database 120 may be filled with spinal column dimensions of desired spinal column curvature. Database 120 may also contain information not only related to the desired spinal column curvature, but also to the achievable spinal column curvature. For example, if, in a previous alignment using a segmented alignment rod or other spinal column alignment device, a 16 year-old patient having severe flatback was unable to achieve spinal column alignment that matched that of the desired or normal curvature for a 16 year-old of that same stature, documentation of the actual achieved curvature may instead be used as the basis for the segmented alignment rod design of a subsequent similar patient. In these instances when it is known that alignment to the normal curvature is unlikely to be achieved, segmented alignment rod creation program 140 may, instead of using the dimensions of a normal spinal column curvature, use an achieved spinal column alignment curvature. By using the achieved spinal column curvature dimensions, the segmented alignment rod may be created to impart less force and thus less discomfort on the deformed spinal column. The dimensions stored in database 120, as they relate to the spinal column, might include upper radius curvature, lower radius curvature, overall spinal column height, number of vertebrae, vertebrae dimensions, disc height, etc. for patients of all ages, heights, sex, and weights.

Input record data 130 is data inputted from a user, for example, patient specific criteria. The user may submit input record data 130, or designate the appropriate data to be provided by the database 120. The system, namely segmented alignment rod creation environment 100, is responsive to input record data 130 provided by a user or read from the database 120. As will be explained in greater detail below, segmented alignment rod creation program 140 receives input record data 130 (and/or data from database 120) and data from imaging machine 150, and generates a segmented alignment rod design, including the number of segments, the dimensions of each of the segments, and dimensions of the rod when all of the segments are fully engaged (e.g., total rod height, upper sagittal curve radius, and lower sagittal curve radius). In some embodiments, input record data 130 includes the patient's age, height, and weight. In some embodiments, input record data 130 further includes the patient's bone density and muscle content, how active the patient is (i.e., normal amounts of daily exercise), diet, dietary restrictions, etc.

Imaging machine 150 is any machine that is capable of taking a detailed image of a patient's spinal column. In some embodiments, imaging machine 150 is capable of taking a detailed image using X-rays, a computed tomography (CT) scan, magnetic resonance imaging (MRI), and/or ultrasound. It should be appreciated, however, that any method suitable for taking a detailed image of a patient's spinal column may be used. Imagine machine 150 takes a detailed image of a patient's spinal column and sends the imagery to segmented alignment rod creation program 140.

Segmented alignment rod creation machine 160 is any machine that is capable of producing a segmented alignment rod using a segmented alignment rod design from segmented alignment rod creation program 140. In some embodiments, segmented alignment rod creation machine 160 comprises a 3D printer or other additive manufacturing machine that creates three-dimensional solid objects from a digital file (i.e., from segmented alignment rod creation program 140). In some embodiments, segmented alignment rod creation machine 160 comprises a computer numerical control (CNC) machine or other subtractive manufacturing machine that creates three-dimensional solid objects from a digital file. It should be appreciated, however, that any method suitable for creating a segmented alignment rod from a custom segmented alignment rod design may be used. Segmented alignment rod creation machine 160 receives a segmented alignment rod design (e.g., in the form of a digital file, dimensions, coordinates, etc.) from segmented alignment rod creation program 140 and manufactures the rod. In some embodiments, segmented alignment rod creation machine 160 forms the entire rod as an integrally formed part and then cuts the integrally formed rod into segments. In some embodiments, segmented alignment rod creation machine 160 forms each segment of the rod separately. FIGS. 10A-B show a customized segmented alignment rod 50. Examples of segmented alignment rod designs are disclosed in U.S. patent application Ser. No. 16/802,695 (Suddaby) and U.S. Pat. No. 10,624,683 (Suddaby), which references are hereby incorporated by reference in their entireties.

Figure 2:
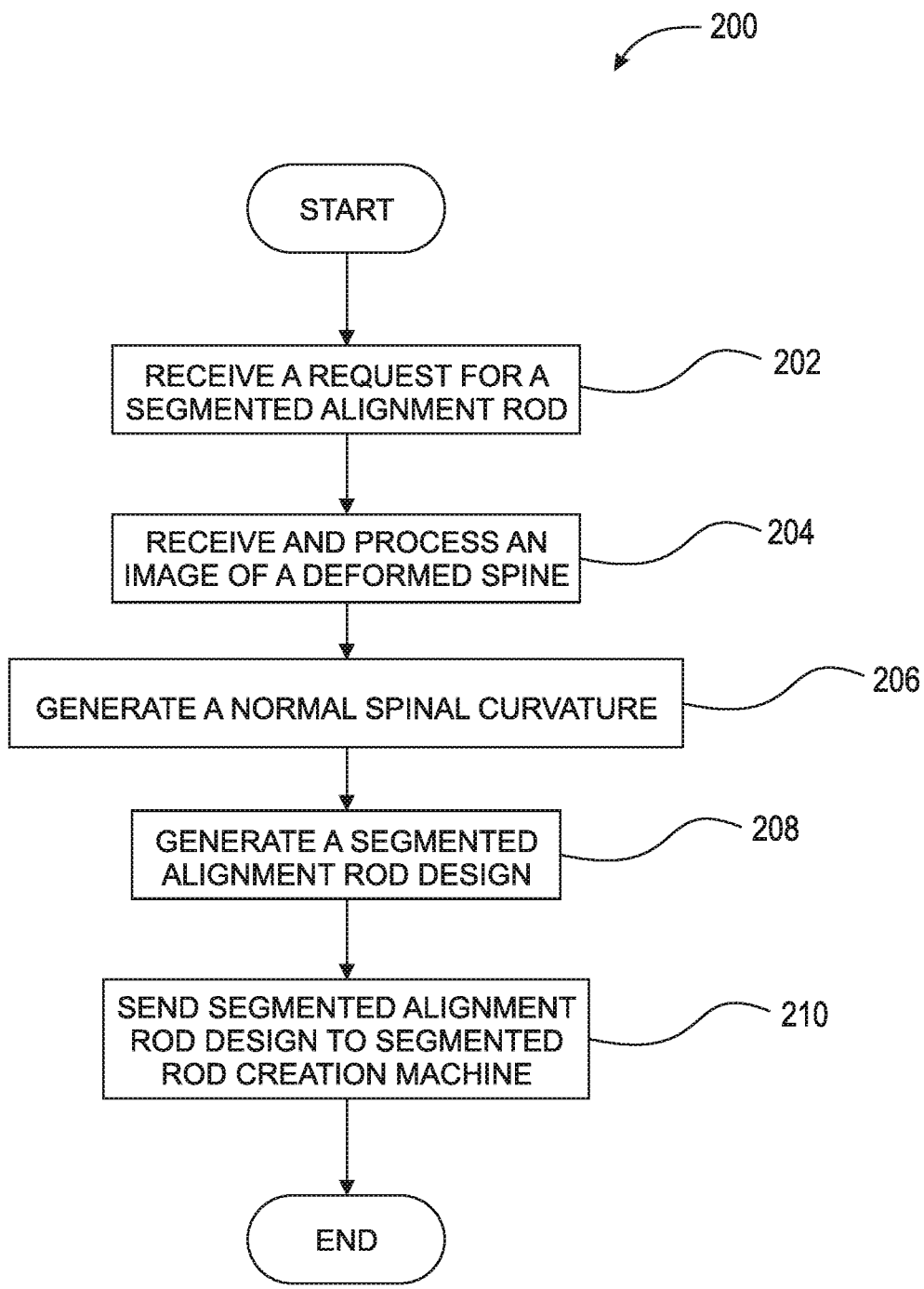
FIG. 2 is a flow chart depicting operational steps for generating a customized segmented alignment rod.

FIG. 2 shows flow chart 200 depicting operational steps for generating/creating a segmented alignment rod customized for a user.

In step 202, segmented alignment rod creation program 140 receives a request for a segmented alignment rod. The request may come from input data 130 in the form of a request as well as other data, for example, and as previously described, a patient's age, height, weight, level of exercise and activeness, muscle content, and any other relevant personal data that may be considered in the creation of a segmented alignment rod or implant. Other data that may be included in the request is a patient's date of birth, previous or recurring health conditions, medications currently being used, or any other relevant health records.

In step 204, segmented alignment rod creation program 140 receives an image of a deformed spine (or spinal column) and processes the image. In some embodiments, segmented alignment rod creation program 140 receives an image of the patient's deformed spine from imaging machine 150 (e.g., from a CT scan). In some embodiments, segmented alignment rod creation program 140 receives an image of the patient's deformed spine from input data 130 (i.e., the imaging was performed by a third party and submitted along with the request in step 202). Various spinal deformities are shown in FIGS. 6A, 7A, 8A, and 9A. In some embodiments, in step 204 or in a subsequent step, segmented alignment rod creation program 140 measures the spinal column from the image of the deformed spine and generates a representative curvature of the spinal column. Segmented alignment rod creation program 140 measures the length of each vertebra and each disc, the overall length of the spinal column (i.e., along its curvature), the height of the spinal column, and the curvature of the spinal column. The length of each vertebra and its adjacent disc is important and is used by segmented alignment rod creation program 140 to generate the length of the segment of the segmented alignment rod that is to be arranged proximate and/or adjacent that vertebra and disc. For example, using the imagery obtained from imaging machine 150, segmented alignment rod creation program 140 may use a calibrated ruler or other computer-aided measuring device to measure the various relevant dimensions of the deformed spinal column (vertebral length, disc height, curvature, spinal column height, etc.). It should be appreciated that any suitable method of measuring a spinal column may be used, for example, the methods disclosed in *A comparison of three methods for measuring thoracic kyphosis: implications for clinical studies*, Goh et al., Oxford Academic (2000) (https://academic.oup.com/rheumatology/article/39/3/310/1783798) and *The growing spine: how spinal deformities influence normal spine and thoracic cage growth*, Dimeglio et al., National Center for Biotechnology Information (2011) (https://www.ncbi.nlm.nih.gov/pmc/articles/PMC3252439/), which references are incorporated herein by reference in their entireties.

Figures 6A, 6B:
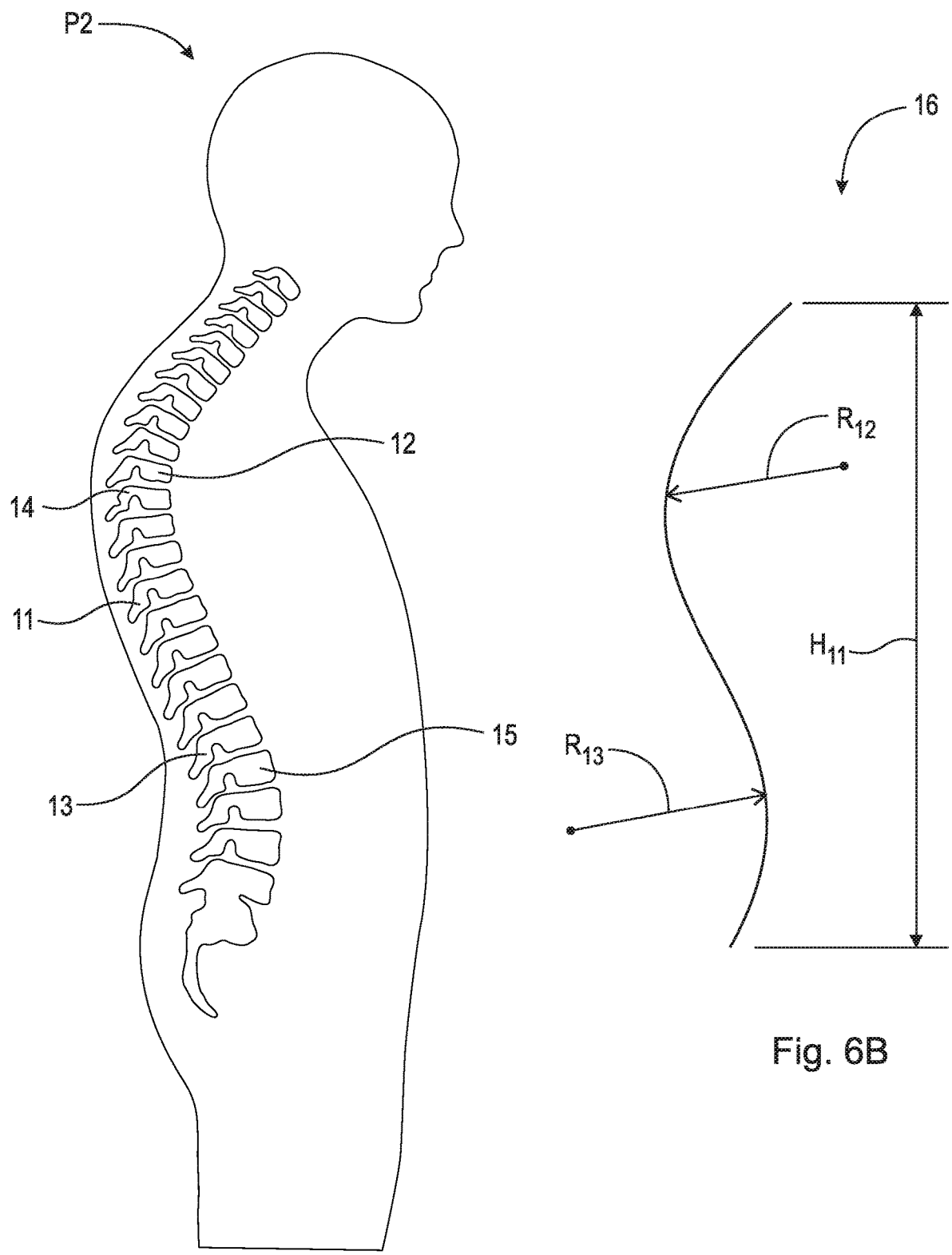
FIG. 6A is a stylized lateral view of a person with a spine afflicted with kyphosis.
FIG. 6B is a line indicating the sagittal curvature of the spine shown in FIG. 6A.

As shown in FIGS. 6A-B, segmented alignment rod creation program 140 receives an image of deformed spinal column 11 of person P2, in this case indicating kyphosis. Spinal column 11 includes vertebrae, and discs arranged between the vertebrae, arranged having upper curve 12 and lower curve 13. As shown, kyphosis is an exaggerated, forward rounding of the back that may result in a decreased upper curve radius $R_{12}$ (i.e., upper curve 12 is more substantial). Segmented rod alignment creation program 140, in step 204, measures the height of each vertebra and disc, the extent of upper curve 12 (i.e., the radius, angle, horizontal position of an apex, etc.), and the extent of lower curve 13 (i.e., the radius, angle, horizontal position of an apex, etc.). In some embodiments, segmented rod alignment creation program 140, in step 204, identifies one or more apex or marked vertebrae, namely, vertebrae 14 and 15. The apex or marked vertebrae are indicated for at least two reasons: 1) segmented alignment rod creation program 140 may include a plurality of segments to be arranged proximate the apex or marked vertebrae, which would allow for maximum displacement and is desirable for a portion of the spinal column that is set to displace the most over time (i.e., in FIG. 6A, apex vertebra 14 must be pulled to the right significantly to properly align spinal column 11); and 2) segmented alignment rod creation program 140 may indicate to the doctor that the segmented alignment rod should be connected or clamped to the apex or marked vertebrae. In some embodiments, segmented alignment rod creation program 140 may generate a representative curvature. For example, as shown in FIG. 6B, a representative sagittal plane curvature 16 has been generated and shows some of the measurements taken by segmented alignment rod creation program 140, namely, upper curve radius $R_{12}$, lower curve radius $R_{13}$, and spinal column height $H_{11}$. The length of each vertebra and disc in spinal column 11 is also measured by segmented alignment rod creation program 140. It should be appreciated that any known system for measuring the spinal column, including vertebral and disc height, may be used (e.g., SURGIMAP® medical imaging software, MEDICREA® imaging software, etc.).

Figure 7A:
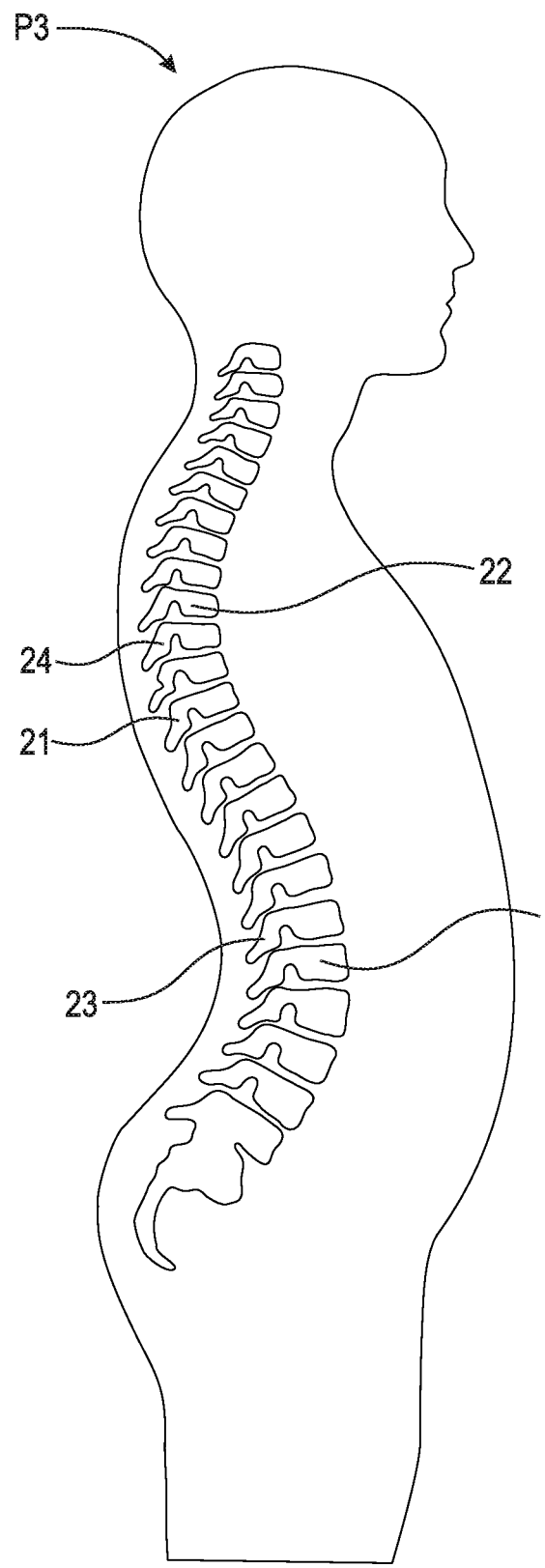
FIG. 7A is a stylized lateral view of a person with a spine afflicted with lordosis.
Figure 7B:
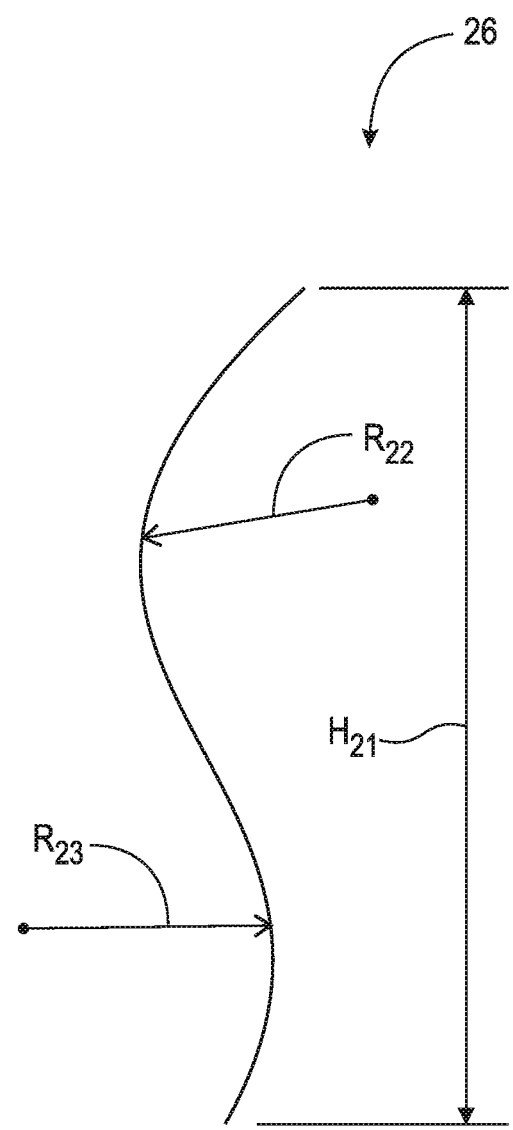
FIG. 7B is a line indicating the sagittal curvature of the spine shown in FIG. 7A.

As shown in FIGS. 7A-B, segmented alignment rod creation program 140 receives an image of deformed spinal column 21 of person P3, in this case indicating lordosis. Spinal column 21 includes vertebrae, and discs arranged between the vertebrae, arranged having upper curve 22 and lower curve 23. As shown, lordosis is an excessive inward curve of the spine that may result in a decreased lower curve radius $R_{23}$ (i.e., lower curve 23 is more substantial). Segmented rod alignment creation program 140, in step 204, measures the height of each vertebra and disc, the extent of upper curve 22 (i.e., the radius, angle, horizontal position of an apex, etc.), and the extent of lower curve 23 (i.e., the radius, angle, horizontal position of an apex, etc.). In some embodiments, segmented rod alignment creation program 140, in step 204, identifies one or more apex or marked vertebrae, for example, vertebrae 24 and 25, for reasons described previously (i.e., in FIG. 7A, apex vertebra 25 must be pulled to the left significantly to properly align spinal column 21). In some embodiments, segmented alignment rod creation program 140 may generate a representative curvature, for example, a representative sagittal plane curvature 26, as shown in FIG. 7B, has been generated and shows some of the measurements taken by segmented alignment rod creation program 140, namely, upper curve radius $R_{22}$, lower curve radius $R_{23}$, and spinal column height 1121. The length of each vertebra and disc in spinal column 21 is also measured by segmented alignment rod creation program 140.

Figures 8A, 8B:
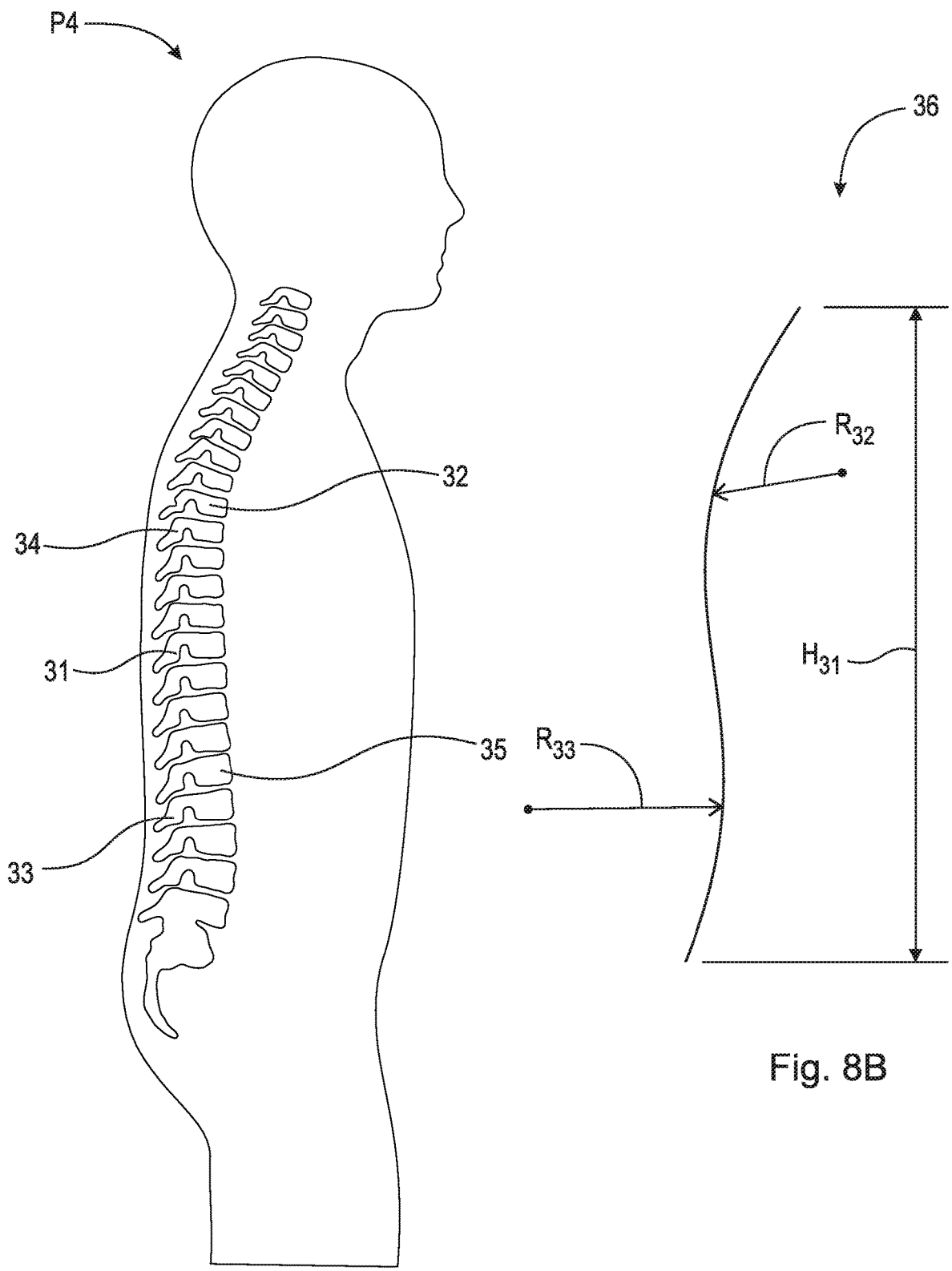
FIG. 8A is a stylized lateral view of a person with a spine afflicted with flat back.
FIG. 8B is a line indicating the sagittal curvature of the spine shown in FIG. 8A.

As shown in FIGS. 8A-B, segmented alignment rod creation program 140 receives an image of deformed spinal column 31 of person P4, in this case indicating flatback. Spinal column 31 includes vertebrae, and discs arranged between the vertebrae, arranged having upper curve 32 and lower curve 33. As shown, flatback syndrome is a condition in which the lower spine loses some of its normal curvature thereby resulting in an increased lower curve radius $R_{33}$ (i.e., lower curve 33 is less substantial). Segmented rod alignment creation program 140, in step 204, measures the height of each vertebra and disc, the extent of upper curve 32 (i.e., the radius, angle, horizontal position of an apex, etc.), and the extent of lower curve 33 (i.e., the radius, angle, horizontal position of an apex, etc.). In some embodiments, segmented rod alignment creation program 140, in step 204, identifies one or more apex or marked vertebrae, for example, vertebrae 34 and 35, for reasons described previously (i.e., in FIG. 8A, apex vertebra 35 must be pulled to the right significantly to properly align spinal column 31). In some embodiments, segmented alignment rod creation program 140 may generate a representative curvature, for example, a representative sagittal plane curvature 36, as shown in FIG. 8B, has been generated and shows some of the measurements taken by segmented alignment rod creation program 140, namely, upper curve radius $R_{32}$, lower curve radius $R_{33}$, and spinal column height 1131. The length of each vertebra and disc in spinal column 31 is also measured by segmented alignment rod creation program 140.

Figures 9A, 9B:
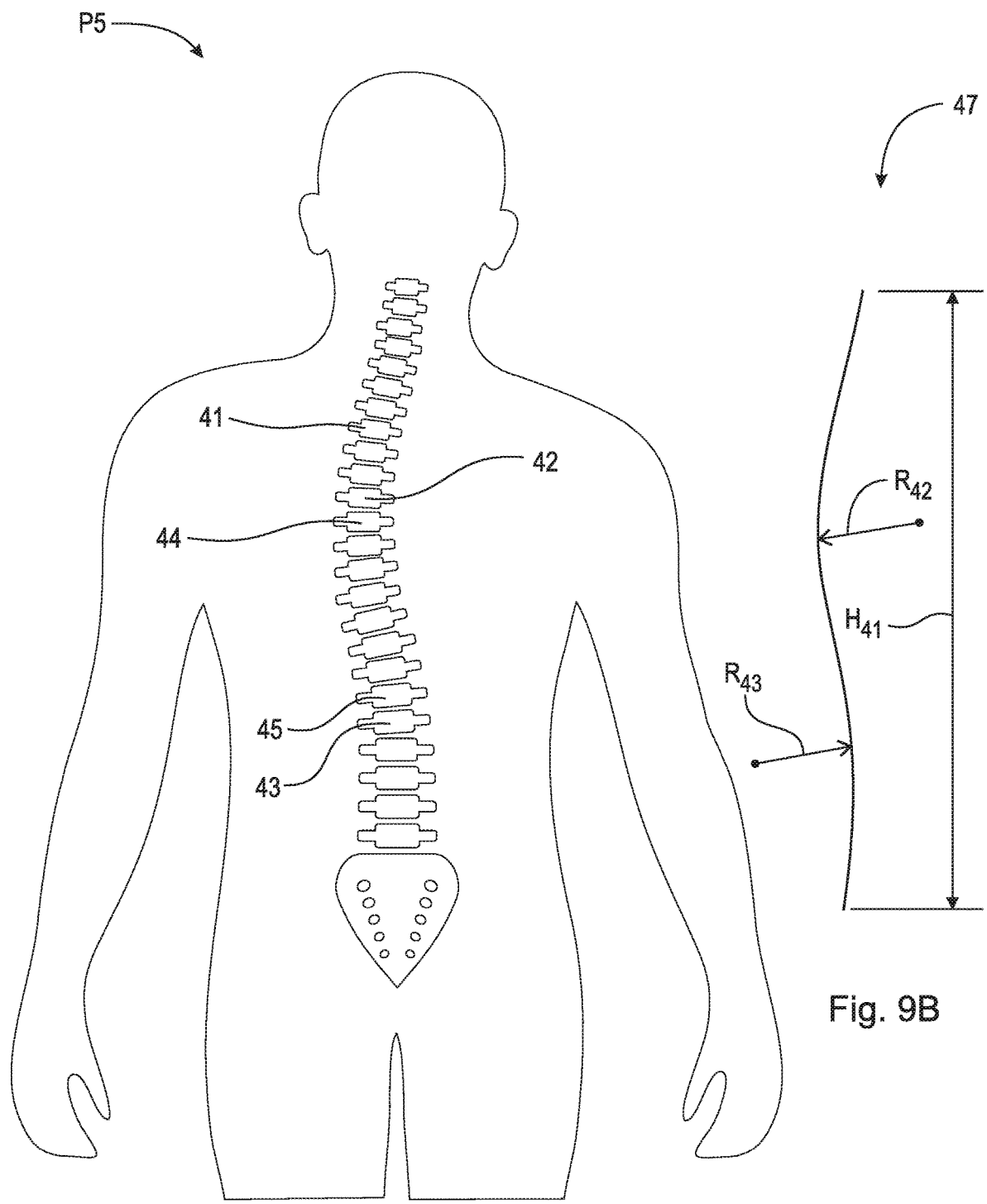
FIG. 9A is a stylized posterior view of a person with a spine afflicted with scoliosis.
FIG. 9B is a line indicating the frontal curvature of the spine shown in FIG. 9A.

As shown in FIGS. 9A-B, segmented alignment rod creation program 140 receives an image of deformed spinal column 41 of person P5, in this case indicating scoliosis. Spinal column 41 includes vertebrae, and discs arranged between the vertebrae, arranged having upper curve 42 and lower curve 43. As shown, scoliosis is curvature in the spine in the frontal plane, thereby creating unwanted curvature, namely, upper curve radius $R_{42}$ and lower curve radius $R_{43}$, in what should be an otherwise straight arrangement. Segmented rod alignment creation program 140, in step 204, measures the height of each vertebra and disc, the extent of upper curve 42 (i.e., the radius, angle, horizontal position of an apex, etc.), and the extent of lower curve 43 (i.e., the radius, angle, horizontal position of an apex, etc.). In some embodiments, segmented rod alignment creation program 140, in step 204, identifies one or more apex or marked vertebrae, for example, vertebrae 44 and 45, for reasons described previously (i.e., in FIG. 9A, apex vertebra 44 must be pulled to the right significantly to properly align spinal column 41). In some embodiments, segmented alignment rod creation program 140 may generate a representative curvature, for example, a representative frontal plane curvature 47, as shown in FIG. 9B, has been generated and shows some of the measurements taken by segmented alignment rod creation program 140, namely, upper curve radius $R_{42}$, lower curve radius $R_{43}$, and spinal column height 1141. The length of each vertebra and disc in spinal column 41 is also measured by segmented alignment rod creation program 140.

Figures 5A, 5B:
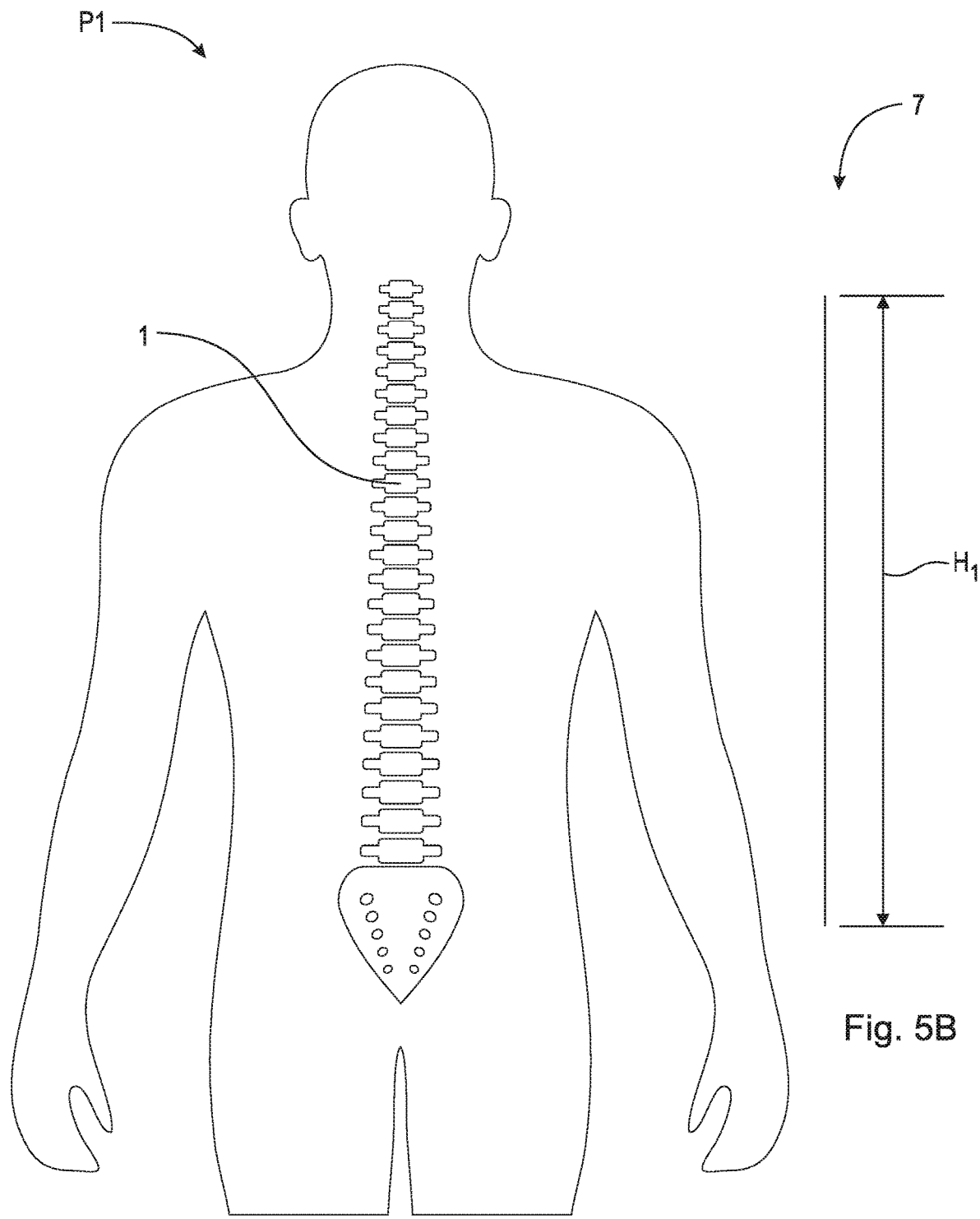
FIG. 5A is a stylized posterior view of a person with a normal spine.
FIG. 5B is a line indicating the frontal curvature of the spine shown in FIG. 5A.

In step 206, segmented alignment rod creation program 140 generates a normal spinal curvature specific to the patient. The normal spinal curvature is generated based, in part, on the patient's age, height, weight, etc. that was received in step 202 via input data 130. Segmented alignment rod creation program 140 communicates with database 120 and generates a normal spinal curvature for a patient having that age, height, weight, etc. For example, FIGS. 4A-B show a possible normal spinal curvature that segmented alignment rod creation program 140 would use to generate a normal spinal curvature for a patient. FIG. 4A shows spinal column 1 of person P1 having upper curve 2, lower curve 4, and apex or marked vertebrae 4 and 5. FIG. 4B shows a representative sagittal plane curvature 6 and some of the relevant dimensions to be used by segmented alignment rod creation program 140 in the creation of the segmented alignment rod, namely, upper curve radius $R_2$, lower curve radius $R_3$, and spinal column height $H_1$. Similarly, FIGS. 5A-B show a normal spinal curvature in the frontal plane. FIG. 5A shows spinal column 1 of person P1. FIG. 5B shows a representative frontal plane curvature 7 and some of the relevant dimensions to be used by segmented alignment rod creation program 140 in the creation of the segmented alignment rod, namely, spinal column height $H_1$. It should be appreciated that while FIG. 5A shows spinal column 1 being substantially linear, some curvature in the spinal column in the frontal plane may be considered normal and thus segmented alignment rod creation program 140 could allow some curvature in the frontal pane when designing the normal curvature. As previously described, in some embodiments, segmented alignment rod creation program 140 may generate a normal spinal curvature based on an achieved spinal column curvature. For example, in a very extreme case of kyphosis, it may be nearly impossible to create a normal curvature and to attempt to force the spinal column into that normal curvature could be detrimental. As such, segmented alignment rod creation program 140 may then choose, in extreme cases (i.e., when upper curve radius $R_{12}$ in FIG. 6B is very small), to generate a spinal curvature that has been successfully achieved in a previous patient with a similar extreme curvature.

In step 208, segmented alignment rod creation program 140, generates a segmented alignment rod design, namely, segmented alignment rod design 50 as shown in FIGS. 10A-B. Segmented alignment rod creation program 140 uses the measurements of the deformed spine taken in step 204 and the normal spinal curvature created in step 206 to create a segmented alignment rod design. As previously described, segmented alignment rod creation program 140 uses the height of the vertebrae and discs in the deformed spinal column to design each segment of segmented alignment rod design 50. As shown, segmented rod design 50 comprises cranial end 51, caudal end 52, and plurality of segments 53A-M. Segments 53A-M comprise lengths 58A-M, respectively. In some embodiments, the length of each segment corresponds to the height of the intended adjacently arranged vertebra and disc (i.e., one segment is the length of one vertebra plus one disc). Since the height of vertebrae and discs differ substantially based on location within the spinal column, for example, in the cervical, thoracic, and lumbar regions, as well as from patient to patient, it is important that the measurements taken in step 204 be accurate.

In some embodiments, segmented alignment rod creation program 140 uses the height of the intended adjacently arranged vertebra and disc and an estimated growth to generate the length of each segment. Since it is known that the spinal column will increase in length as the patient grows, segmented alignment rod creation program 140 estimates the vertebral and disc height at terminal growth, or at the point where the spinal column ceases to grow. This estimation is based, at least in part, on patient data in database 120. In some embodiments, segmented alignment rod creation program 140 will retrieve the dimensions of a patient of a similar age, height, weight, vertebral and disc height, etc., determine the total growth of that patient's spinal column length (i.e., vertebral and disc height) from that age until terminal growth, and use that total increased length/growth to create segmented alignment rod design 50. For example, segmented alignment rod creation program 140 calculates the estimated growth in terms of length, divides that length by the number of segments in segmented rod design 50, and adds that length amount to each segment. As an example, consider the following: segmented alignment rod creation program 140 designs segmented alignment rod design 50 to have five segments. Each of the segments corresponds to one vertebra and one disc totaling a height of 5 centimeters. Thus, each segment must be at least five centimeters in length. Segmented alignment rod creation program 140 further estimates that the spinal column will grow 15 centimeters in length before terminal growth is reached. As such, segmented alignment rod creation program 140 adds 3 centimeters of length to each of the five segments such that each segment is 8 inches long (15 centimeters of estimated growth divided by 5 total segments).

In some embodiments, segmented alignment rod creation program 140 uses measurements of the deformed spine taken in step 204 and the normal spinal curvature created in step 206 to create a segmented alignment rod design, specifically, the exact dimensions and characteristics of each segment. Each segmented of segmented rod design 50 may have a specific shape or curvature based on where they fit in on the calculated rod shape. Additionally, the physical interactions between the individual segments is such that, when fit together, permits limited desirable motion therebetween or eliminates motion therebetween altogether. For example, a segment to be arranged in the mid-thoracic portion of the segmented alignment rod should have a greater curvature (if any) than a segment to be arranged in the lower thoracic portion. This shape change and curvature may be addressed by either creating a curved individual segment or altering the male/female engaging elements, or both. As the segmented alignment rod gradually aligns, by virtue of the segments being brought closer together, so too does the tightness of the fit between male and female engaging elements with increasing limits on movement between adjacent segments until little or no movement therebetween remains. In some cases, one or more degrees of movement between segments is desirable, even when final tautness in the segmented alignment rod is achieved (i.e., the line or cable running through the segments reaches its maximum desired tautness to pull the segments of the segmented alignment rod into full engagement). This degree of movement between segments is desirable for two reasons: 1) to allow normal movement of the spine while and after it is aligned; and, 2) to reduce stress on the spine rod interface where the alignment force is applied (i.e., such stress on a rigid rod would cause the rigid rod to fail).

FIG. 11A is a perspective view of segment 62 of a segmented alignment rod. FIG. 11B is a side elevational view of segment shown 62. Segment 62 is an example embodiment of a segment of segmented alignment rod assembly 50. As shown, segment 62 comprises a generally ovular cross-section; although it should be appreciated that any suitable geometry may be used, such as, for example, circular, ellipsoidal, square, rectangular, triangular, trapezoidal, polynomial, etc. Segment 62 comprises body 64, end 66, end 68, male engaging element 70, and female engaging element 72.

Male engaging element 70 is connected to end 68 and tapers therefrom. Male engaging element 70 is operatively arranged to engage the female engaging element of the adjacent segment. Male engaging element 70 comprises axial length L and taper angle $\alpha$. By varying length L and angle $\alpha$, the angle of movement between segments can also be defined. For example as angle $\alpha$ increases, the movement and/or flexion between segment 62 and the adjacent segment connected to end 68 also increases. As angle $\alpha$ decreases or becomes "steeper," the movement and/or flexion between segment 62 and the adjacent segment connected to end 68 decreases. Similarly, as length L decreases, less surface area of male engaging element 70 is in contact with the surface area of the female engaging element of the adjacent segment, and thus movement and/or flexion between the segment 62 and the adjacent segment connected to end 68 increases. As length L increases, more surface area of male engaging element 70 can contact with the surface area of the female engaging element of the adjacent segment, and thus movement and/or flexion between the segment 62 and the adjacent segment connected to end 68 decreases.

Female engaging element 72 is connected to end 66 and tapers therefrom within body 64. Female engaging element 72 is operatively arranged to engage the male engaging element of the adjacent segment. Female engaging element 72 comprises taper angle $\beta$. It should be appreciated that taper angle $\alpha$ and taper angle $\beta$ do not necessarily need to be the same, but they can be. segmented alignment rod creation program 140 may design segmented alignment rod design 50 to have varying degrees of movement and/or flexion at different sections of the rod. However, taper angles of engageable male and female engaging members should be the same for proper engagement and alignment. In some embodiments, taper angle $\beta$ is equal to the male engaging member taper angle of the adjacent segment. In some embodiments, taper angle $\beta$ is not equal to the male engaging member taper angle of the adjacent segment.

As previously described, body 64 may comprise a curvature. As shown, body 64 comprises inner radius $R_I$ and outer radius $R_O$. Such curvature and radii corresponds to the desired final curvature of the segmented alignment rod 50 and thus the spinal column.

Figure 13:
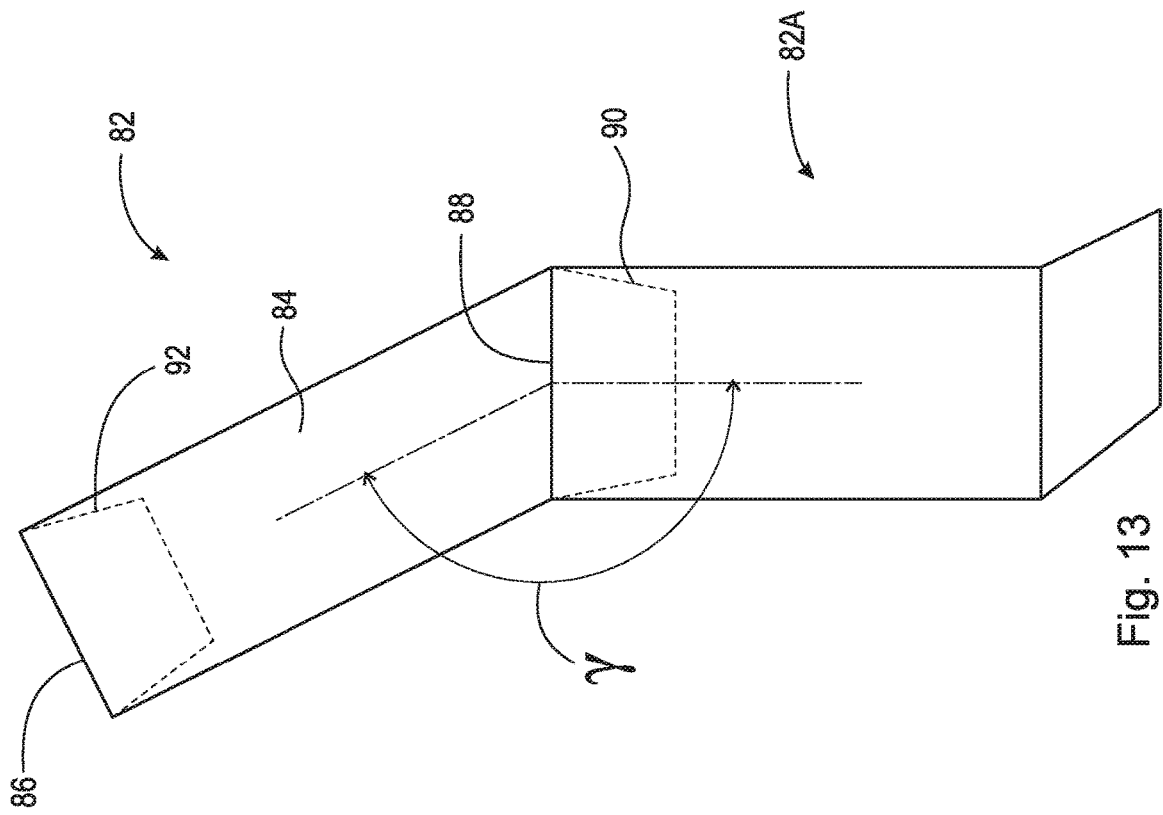
FIG. 13 is a side elevational view of the segment shown in FIG. 12, engaged with an adjacent segment of the segmented alignment rod.
Figure 12:
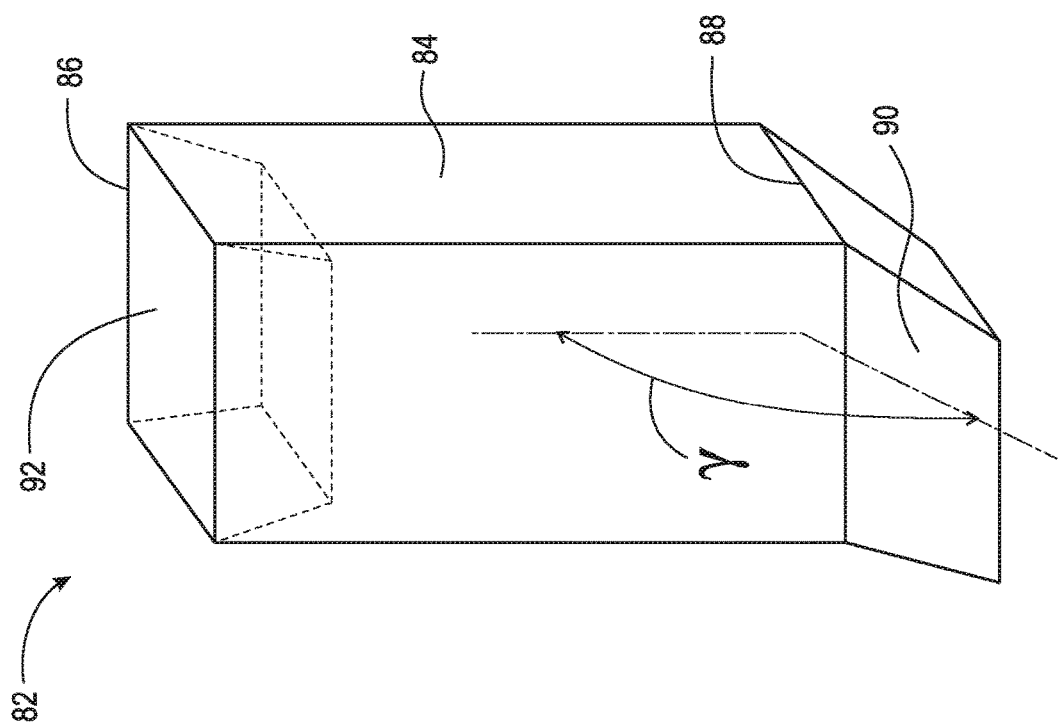
FIG. 12 is a perspective view of a segment of a segmented alignment rod.

In some embodiments, the tapered male engaging element or the female tapered male engaging element may be shaped or designed such that it is the engaging elements that form the curvature of segmented alignment rod 50. FIG. 12 is a perspective view of segment 82 of a segmented alignment rod. FIG. 13 is a side elevational view of segment 82 engaged with adjacent segment 82A of the segmented alignment rod. Segments 82 and 82A are example embodiments of segments of segmented alignment rod assembly 50. As shown, segment 82 comprises a generally square cross-section; although it should be appreciated that any suitable geometry may be used, such as, for example, ovular, ellipsoidal, rectangular, triangular, trapezoidal, circular, polynomial, etc. Segment 82 comprises body 84, end 86, end 88, male engaging element 90, and female engaging element 92.

Male engaging element 90 is connected to end 88 and tapers therefrom. Male engaging element 90 is operatively arranged to engage the female engaging element of the adjacent segment, for example, segment 82A. Male engaging element 90 comprises an axial length and a taper angle, as previously described with respect to FIGS. 11A-B. Male engaging element 90 is also arranged at an angle with respect to body 84. Specifically, a centerline of male engaging element 90 is arranged at angle $\gamma$ with respect to a centerline of body 84. This angled segment design allows the junction or the engagement of segments to dictate the curvature of segmented alignment rod design 50. This is best shown in FIG. 13, wherein segment 82 is fully engaged with segment 82A. Body 84 of segment 82 and the body of segment 82A are substantially linear. However, the shape of male engaging element 90, namely, male engaging element 90 be arranged at angle $\gamma$ with respect to body 84, results in a curved or angled segmented alignment rod (i.e., when fully engaged, substantially linear segments 82 and 82A are arranged at an angle or form a curvature).

Female engaging element 92 is connected to end 86 and tapers therefrom within body 84. Female engaging element 82 is operatively arranged to engage the male engaging element of the adjacent segment. In some embodiments, female engaging member 92 is arranged at an angle or curvature from a centerline of body 84 such that the shape of female engaging member 92, when engaged with the male engaging member of the adjacent segment, forms the curvature of segmented alignment rod 50. In some embodiments, both male engaging member 90 and female engaging member 92 are arranged at angles from a centerline of body 84.

Segmented alignment rod design 50 further comprises upper curve radius 54, lower curve radius 55, and height 56. As previously described, segmented alignment rod creation program 140 designs segmented alignment rod design 50 according to a normal spinal column curvature or an achievable spinal column curvature. In some embodiments, segmented alignment rod creation program 140 designs segmented alignment rod design 50 to have upper curve radius 54 equal to upper curve radius $R_2$, lower curve radius 55 equal to lower curve radius $R_3$, and height 56 equal to height $H_1$, as in the dimensions of normal person P1 as shown in FIGS. 4A-5B. It should be appreciated that FIGS. 10A-B show segmented alignment rod design 50 with segments 53A-M fully engaged with each other (i.e., segmented alignment rod design 50 is in its final shape after having been fully tensioned by a tensioning mechanism). The means engaging segments 53A-M are known in the art, and may include tapered portions, tangs, or any other suitable engagement means. Segmented alignment rod design 50 may further include aperture 57. In some embodiments, aperture 57 extends completely through segmented alignment rod 50 (i.e., through each of segments 53A-M). In some embodiments, aperture 57 extends at least partially through segmented alignment rod 50. A tensioning device may gradually pull the separated segments 53A-M into engagement, which in turn straightens the deformed spinal column. It should be appreciated that the various segments of the present disclosure may be hollow or may be solid having a through-bore through which the tensioning member(s) extends. It should also be appreciated that the various segments of the present disclosure may include a plurality of through-bores through which a plurality of tensioning members extend. In some embodiments, segmented alignment rod creation program 140 indicates one or more of segments 53A-M as being a marked segment. The indicated marked segment is intended to be clamped to a vertebra, for example, a marked or apex vertebra. In some embodiments, the marked segments are to be created with an attachment point, to be attached to a clamp or screw. In some embodiments, the marked segments have a marking or color indicator. It should be appreciated that any suitable means for indicating that a segment is to be a marked vertebra may be used. Various segments engagement means and tensioning methods have been disclosed in U.S. patent application Ser. No. 16/802,695 (Suddaby) and U.S. Pat. No. 10,624,683 (Suddaby), which references are incorporated by reference herein.

In step 210, segmented alignment rod creation program 140 sends segmented alignment rod design 50 to segmented alignment rod creation machine 160 to be manufactured. As previously described, segmented alignment rod creation machine 160 may be a 3D printer or other additive manufacturing machine that creates three-dimensional solid objects from a digital file (i.e., from segmented alignment rod creation program 140). In some embodiments, segmented alignment rod creation machine 160 comprises a CNC machine or other subtractive manufacturing machine that creates three-dimensional solid objects from a digital file. It should be appreciated, however, that any method suitable for creating a segmented alignment rod from a custom segmented alignment rod design may be used. Segmented alignment rod creation machine 160 receives a segmented alignment rod design (e.g., in the form of a digital file, dimensions, coordinates, etc.) from segmented alignment rod creation program 140 and manufactures the rod. In some embodiments, segmented alignment rod creation machine 160 forms the entire rod as an integrally formed part and then cuts the integrally formed rod into segments. In some embodiments, segmented alignment rod creation machine 160 forms each segment of the rod separately. It should be appreciated that the segmented alignment rod that is created by segmented alignment rod creation program 140 is arranged to be implanted into a patient with the segmented thereof in a separated arrangement, and overtime, the segments are pulled together into engagement with each other to form a semi-rigid rod. By semi-rigid, it is meant that the segmented alignment rod will, when the segments thereof are fully engaged, allow substantial degrees of normal movement by the patient. Thus, the segmented alignment rod of the present disclosure differs substantially form a solid alignment rod, which permits no normal movement by the patient. Additionally, the segmented alignment rod of the present disclosure is flexible upon implantation and thus may be easier to implant than a solid rod. It should also be appreciated that the segmented alignment rod of the present invention can be altered in an operating room at the time of surgery (e.g., if the segmented rod must be shortened, a doctor may simply remove segments therefrom), whereas solid rods do not have such capabilities (i.e., solid metal rods are manufactured off site and cannot be altered at the time of surgery).

Figure 3:
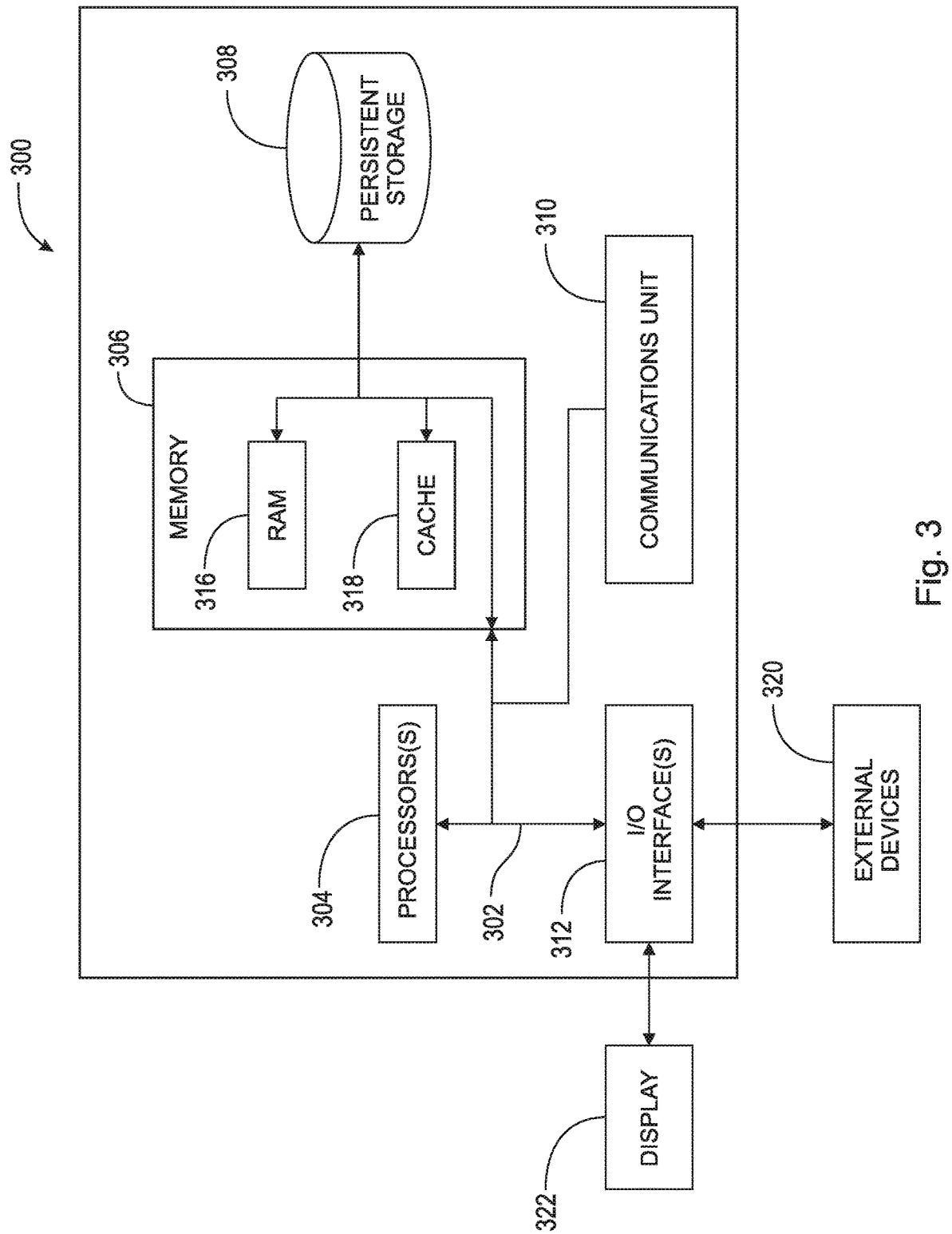
FIG. 3 is a block diagram of internal and external components of a computer system, in accordance with some embodiments of the present disclosure.

FIG. 3 is a block diagram of internal and external components of computing device 300, which is representative of the computing device of FIG. 1, in accordance with an embodiment of the present disclosure. It should be appreciated that FIG. 3 provides only an illustration of one implementation and does not imply any limitations with regard to the environments in which different embodiments may be implemented. In general, the components illustrated in FIG. 3 are representative of any electronic device capable of executing machine-readable program instructions. Examples of computer systems, environments, and/or configurations that may be represented by the components illustrated in FIG. 3 include, but are not limited to, personal computer systems, server computer systems, thin clients, thick clients, laptop computer systems, tablet computer systems, cellular telephones (i.e., smart phones), multiprocessor systems, microprocessor-based systems, network PCs, minicomputer systems, mainframe computer systems, and distributed cloud computing environments that include any of the above systems or devices.

Computing device 300 includes communications fabric 302, which provides for communications between one or more processing units 304, memory 306, persistent storage 308, communications unit 310, and one or more input/output (I/O) interfaces 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses.

Memory 306 and persistent storage 308 are computer readable storage media. In this embodiment, memory 306 includes random access memory (RAM) 316 and cache memory 318. In general, memory 306 can include any suitable volatile or non-volatile computer readable storage media. Software is stored in persistent storage 308 for execution and/or access by one or more of the respective processors 304 via one or more memories of memory 306.

Persistent storage 308 may include, for example, a plurality of magnetic hard disk drives. Alternatively, or in addition to magnetic hard disk drives, persistent storage 308 can include one or more solid state hard drives, semiconductor storage devices, read-only memories (ROM), erasable programmable read-only memories (EPROM), flash memories, or any other computer readable storage media that is capable of storing program instructions or digital information.

The media used by persistent storage 308 can also be removable. For example, a removable hard drive can be used for persistent storage 308. Other examples include optical and magnetic disks, thumb drives, and smart cards that are inserted into a drive for transfer onto another computer readable storage medium that is also part of persistent storage 308.

Communications unit 310 provides for communications with other computer systems or devices via a network. In this exemplary embodiment, communications unit 310 includes network adapters or interfaces such as a TCP/IP adapter cards, wireless Wi-Fi interface cards, or 3G or 4G wireless interface cards or other wired or wireless communications links. The network can comprise, for example, copper wires, optical fibers, wireless transmission, routers, firewalls, switches, gateway computers and/or edge servers. Software and data used to practice embodiments of the present disclosure can be downloaded to computing device 300 through communications unit 310 (i.e., via the Internet, a local area network, or other wide area network). From communications unit 310, the software and data can be loaded onto persistent storage 308.

One or more I/O interfaces 312 allow for input and output of data with other devices that may be connected to computing device 300. For example, I/O interface 312 can provide a connection to one or more external devices 320 such as a keyboard, computer mouse, touch screen, virtual keyboard, touch pad, pointing device, or other human interface devices. External devices 320 can also include portable computer readable storage media such as, for example, thumb drives, portable optical or magnetic disks, and memory cards. I/O interface 312 also connects to display 322.

Display 322 provides a mechanism to display data to a user and can be, for example, a computer monitor. Display 322 can also be an incorporated display and may function as a touch screen, such as a built-in display of a tablet computer.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

P1 Person
P2 Person
P3 Person
P4 Person
P5 Person
1 Spinal column
2 Upper curve
3 Lower curve
4 Apex vertebra
5 Apex vertebra
6 Representative sagittal (plane) curvature
7 Representative frontal (plane) curvature
11 Spinal column
12 Upper curve
13 Lower curve
14 Apex vertebra
15 Apex vertebra
16 Representative sagittal (plane) curvature
21 Spinal column
22 Upper curve
23 Lower curve
24 Apex vertebra
25 Apex vertebra
26 Representative sagittal (plane) curvature
31 Spinal column
32 Upper curve
33 Lower curve
34 Marked or apex vertebra
35 Marked or apex vertebra
36 Representative sagittal (plane) curvature
41 Spinal column
42 Upper curve
43 Lower curve
44 Marked or apex vertebra
45 Marked or apex vertebra
46 Representative frontal (plane) curvature
50 Segmented alignment rod design (segmented alignment rod)
51 Cranial end
52 Caudal end
53A Segment
53B Segment
53C Segment
53D Segment
53E Segment
53F Segment
53G Segment
53H Segment
53I Segment
53J Segment
53K Segment
53L Segment
53M Segment
54 Upper curve radius
55 Lower curve radius
56 Height
57 Aperture
58A Length
58B Length
58C Length
58D Length
58E Length
58F Length
58G Length
58H Length
58I Length
58J Length
58K Length
58L Length
58M Length
62 Segment
64 Body
66 End
68 End
70 Engaging element
72 Engaging element
82 Segment
82A Segment
84 Body
86 End
88 End
90 Engaging element
92 Engaging element
100 Segmented alignment rod creation environment
110 Network
120 Database
130 Input record data
140 Segmented alignment rod creation program 150 Imaging machine
160 Segmented alignment rod creation machine
200 Flow chart
202 Step
204 Step
206 Step
208 Step
210 Step
300 Computing device
302 Communications fabric
304 Processing units
306 Memory
308 Persistent storage
310 Communications unit
312 Input/output (I/O) interfaces
316 Random access memory (RAM)
318 Cache memory
320 External device(s)
322 Display
$H_1$ Spinal column height
$H_{11}$ Spinal column height
$H_{21}$ Spinal column height
$H_{31}$ Spinal column height
$H_{41}$ Spinal column height
$R_2$ Upper curve radius
$R_3$ Lower curve radius
$R_{12}$ Upper curve radius
$R_{13}$ Lower curve radius
$R_{22}$ Upper curve radius
$R_{23}$ Lower curve radius $R_{32}$ Upper curve radius
$R_{33}$ Lower curve radius
$R_{42}$ Upper curve radius
$R_{43}$ Lower curve radius
$R_I$ Radius
$R_O$ Radius
L Length
α Angle
β Angle
γ Angle

What is claimed is:

1. A method for creating a segmented alignment rod, the method comprising:
  receiving a request for a segmented alignment rod;
  receiving at least one image of a deformed spine;
  generating a normal spinal curvature; and,
  generating a segmented alignment rod design including at least a first segment and a second segment arranged to be removably engaged with the first segment.

2. The method as recited in claim 1, further comprising:
  sending the segmented alignment rod design to a segmented alignment rod creation machine.

3. The method as recited in claim 1, further comprising, after the step of receiving the at least one image of the deformed spine:
  measuring the deformed spine.

4. The method as recited in claim 3, wherein the step of measuring the deformed spine comprises:
  measuring one or more vertebra and one or more discs of the deformed spine; and,
  measuring a curvature of the deformed spine.

5. The method as recited in claim 4, wherein the step of generating the segmented alignment rod design comprises:
  based on the at least one image received, determining a number of segments in the segmented alignment rod design; and,
  based on the measurements, determining a length of each of the segments.

6. The method as recited in claim 4, wherein the step of generating the segmented alignment rod design comprises:
  based on the at least one image received, determining a number of segments in the segmented alignment rod design;
  estimating a total length of growth of the deformed spine; and,
  based on the measurements and the estimated total length of growth, determining a length of each of the segments.

7. The method as recited in claim 4, wherein the step of generating the segmented alignment rod design comprises:
  based on the at least one image received, determining a number of segments in the segmented alignment rod design; and,
  based on the measurements and the normal spinal curvature, determining a curvature of each of the segments.

8. The method as recited in claim 4, wherein the step of generating the segmented alignment rod design comprises:
  based on the at least one image received, determining a number of segments in the segmented alignment rod design; and,
  based on the measurements, determining a male engaging element shape and a female engaging element shape for each of the segments.

9. The method as recited in claim 1, wherein the step of generating the segmented alignment rod design comprises:
  based on the at least one image received, determining a number of segments in the segmented alignment rod design and a length of each of the segments.

10. The method as recited in claim 1, wherein the step of receiving the request for the segmented alignment rod comprises:
  receiving data related to a patient.

11. The method as recited in claim 10, wherein the data comprises an age and height.

12. The method as recited in claim 10, wherein the step of generating the normal spinal curvature comprises:
  comparing the data to a plurality of normal spinal curvatures in a database;
  selecting one spinal curvature of the plurality of normal spinal curvatures; and,
  generating the normal spinal curvature based on dimensions of the selected normal spinal curvature.

13. A method for creating a segmented alignment rod including a plurality of segments, the method comprising:
  receiving at least one image of a deformed spine;
  measuring the deformed spine;
  based on the at least one image received, determining a number of segments in the segmented alignment rod design;
  based on the measurements, determining a male engaging element shape and/or a female engaging element shape for each of the plurality of segments;
  generating a normal spinal curvature; and,
  generating a segmented alignment rod design.

* * * * *